(12) United States Patent
George et al.

(10) Patent No.: US 6,334,069 B1
(45) Date of Patent: Dec. 25, 2001

(54) PULSED ELECTROMAGNETIC ENERGY TREATMENT APPARATUS AND METHOD

(75) Inventors: Frank R. George, Scottsdale; Arthur A. Loya, Mesa; Mary C. Ritz, Scottsdale; Robert T. Bryant, Tempe, all of AZ (US)

(73) Assignee: Regenesis Biomedical, Inc., Scottsdale, AZ (US)

( * ) Notice: Subject to any disclaimer, the term of this patent is extended or adjusted under 35 U.S.C. 154(b) by 0 days.

(21) Appl. No.: 09/231,790

(22) Filed: Jan. 15, 1999

Related U.S. Application Data

(60) Provisional application No. 60/071,396, filed on Jan. 15, 1998.

(51) Int. Cl.$^7$ ...................................................... A61N 1/40
(52) U.S. Cl. ................................. 607/2; 607/50; 607/155
(58) Field of Search ..................................... 607/2, 50, 96, 607/101, 103, 149–152, 154, 155; 600/14–15; 606/41

(56) References Cited

U.S. PATENT DOCUMENTS

| | | |
|---|---|---|
| 3,043,310 | 7/1962 | Milinowski et al. . |
| 3,127,895 | 4/1964 | Kendall et al. . |
| 3,181,535 | 5/1965 | Milinowski . |

(List continued on next page.)

FOREIGN PATENT DOCUMENTS

| 0 538 510 | 4/1993 | (EP) . |
|---|---|---|

OTHER PUBLICATIONS

J.H. Goldin et al, "The effects of Diapulse on the healing wounds: a double–blind randomised controlled trial in man", Journal of Plastic Surgery, 1981, 34, pp. 267–270.

Christopher J. Schaffer et al, "Cell Biology of Wound Healing", pp. 151–181, Vanderbilt University School of Medicine, Plastic Surgery Research Laboratories, International Review of Cytology, vol. 169, 1996.

(List continued on next page.)

Primary Examiner—Jeffrey R. Jastrzab
(74) Attorney, Agent, or Firm—Morrison & Foerster LLP

(57) ABSTRACT

A method of and apparatus for the treatment of chronic wounds using pulsed electromagnetic energy provides a constant, known and replicable dosage output which remains unaffected by the capacitance of the patient's body. The apparatus is simple to operate, requiring little operator training or interaction with the apparatus. All specifications of the apparatus relating to the generation and emission of electromagnetic energy are fixed, with the specifications based on actual scientific studies of the various technical parameters involved, such as pulse width and RF dosage. The apparatus includes a pulsed electromagnetic energy generator, a power level controller and one or more thin applicators which can be flexible. The applicators are located immediately adjacent to the patient's body, without the aid of a support member or removal of any dressings or bandages. The generator, which can be battery-operated, is a low power, programmable compact unit whose output is controlled by multiple control circuits for ensuring accurate treatment dosage, for confirming that the treatment was properly administered, and for disabling the generator when appropriate. The generator output is automatically adjusted in response to instructions from the field strength sensor located on or near the applicator. Multiple applicators selected to operate simultaneously at different treatment dosage levels are connected to the generator by multi-conductor cables and readily located directly on the treatment area. Each applicator is a pad including etched printed circuits. The circuits are matched and pre-tuned. An applicator-to-patient proximity detector is also incorporated in or on each applicator and connected to the generator via a power controller to provide for direct monitoring of the treatment site and precise control of treatment dosage.

56 Claims, 14 Drawing Sheets

U.S. PATENT DOCUMENTS

| | | |
|---|---|---|
| 3,299,892 | 1/1967 | Kendall et al. . |
| 3,329,148 | 7/1967 | Kendall et al. . |
| 3,464,010 | 8/1969 | Saul . |
| 3,503,403 | 3/1970 | Yarger . |
| 3,513,851 | 5/1970 | Smith et al. . |
| 3,543,762 | 12/1970 | Kendall et al. . |
| 3,566,877 | 3/1971 | Smith et al. . |
| 3,638,657 | 2/1972 | Mettler . |
| 3,670,737 | 6/1972 | Pearo . |
| 3,800,802 | 4/1974 | Berry et al. . |
| 3,890,953 | 6/1975 | Kraus et al. . |
| 3,893,462 | 7/1975 | Manning . |
| 3,915,151 | 10/1975 | Kraus . |
| 3,952,751 | 4/1976 | Yarger . |
| 3,954,111 | 5/1976 | Sato . |
| 3,978,864 | 9/1976 | Smith et al. . |
| 4,028,518 | 6/1977 | Boudouris et al. . |
| 4,062,365 | 12/1977 | Kameny . |
| 4,066,065 | 1/1978 | Kraus . |
| 4,197,851 | 4/1980 | Fellus . |
| 4,210,152 | 7/1980 | Berry . |
| 4,226,246 | 10/1980 | Fragnet . |
| 4,266,532 | 5/1981 | Ryaby et al. . |
| 4,305,115 | 12/1981 | Armitage . |
| 4,318,411 | 3/1982 | Elmovist . |
| 4,338,945 | 7/1982 | Kosugi et al. . |
| 4,412,540 | 11/1983 | Bentall . |
| 4,429,698 | 2/1984 | Bentall . |
| 4,432,361 | 2/1984 | Christensen et al. . |
| 4,454,883 | 6/1984 | Fellus . |
| 4,467,808 | 8/1984 | Brighton et al. . |
| 4,467,809 | 8/1984 | Brighton . |
| 4,535,775 | 8/1985 | Brighton et al. . |
| 4,548,208 | 10/1985 | Niemi . |
| 4,574,809 | 3/1986 | Talish et al. . |
| 4,587,957 | 5/1986 | Castel . |
| 4,616,626 | 10/1986 | Moore . |
| 4,622,952 | 11/1986 | Gordon . |
| 4,641,633 | 2/1987 | Delgado . |
| 4,654,574 | 3/1987 | Thaler . |
| 4,665,898 | 5/1987 | Costa et al. . |
| 4,671,286 | 6/1987 | Renault . |
| 4,674,482 | 6/1987 | Waltonen et al. . |
| 4,683,873 | 8/1987 | Cadossi et al. . |
| 4,727,878 | 3/1988 | Levine . |
| 4,738,250 | 4/1988 | Fulkerson et al. . |
| 4,757,804 | 7/1988 | Griffith et al. . |
| 4,765,310 | 8/1988 | Deagle et al. . |
| 4,793,325 | 12/1988 | Cadossi et al. . |
| 4,818,697 | 4/1989 | Liboff et al. . |
| 4,895,154 | 1/1990 | Bartelt et al. . |
| 4,919,140 | 4/1990 | Borgens et al. . |
| 4,932,951 | 6/1990 | Liboff et al. . |
| 4,982,742 | 1/1991 | Claude . |
| 4,993,413 | 2/1991 | McLeod et al. . |
| 4,998,532 | 3/1991 | Griffith . |
| 5,000,178 | 3/1991 | Griffith . |
| 5,014,699 | 5/1991 | Pollack et al. . |
| 5,045,050 | 9/1991 | Liboff et al. . |
| 5,059,298 | 10/1991 | Liboff . |
| 5,088,976 | 2/1992 | Liboff et al. . |
| 5,099,756 | 3/1992 | Franconi et al. . |
| 5,099,840 | 3/1992 | Goble et al. . |
| 5,107,835 | 4/1992 | Thomas . |
| 5,117,826 | 6/1992 | Bartelt et al. . |
| 5,123,898 | 6/1992 | Liboff et al. . |
| 5,158,081 | 10/1992 | McWhorter et al. . |
| 5,160,591 | 11/1992 | Liboff et al. . |
| 5,181,902 | 1/1993 | Erickson et al. . |
| 5,183,456 | 2/1993 | Liboff et al. . |
| 5,186,181 | 2/1993 | Franconi et al. . |
| 5,195,940 | 3/1993 | Baylink . |
| 5,195,941 | 3/1993 | Erickson et al. . |
| 5,198,941 | 3/1993 | Erickson et al. . |
| 5,267,938 | 12/1993 | Konotchick . |
| 5,314,401 | 5/1994 | Tepper . |
| 5,338,286 | 8/1994 | Abbott et al. . |
| 5,370,680 | 12/1994 | Proctor . |
| 5,395,398 | 3/1995 | Rogozinski . |
| 5,401,233 | 3/1995 | Erickson et al. . |
| 5,433,735 | 7/1995 | Zanakis et al. . |
| 5,441,495 | 8/1995 | Liboff et al. . |
| 5,478,303 | 12/1995 | Foley-Nolan et al. . |
| 5,480,373 | 1/1996 | Fischer et al. . |
| 5,527,259 | 6/1996 | Grace et al. . |
| 5,549,639 | 8/1996 | Ross . |
| 5,549,640 | 8/1996 | Fontenot . |
| 5,584,863 | 12/1996 | Rauch et al. . |
| 5,634,939 | 6/1997 | Kuster et al. . |
| 5,776,175 | 7/1998 | Eckhouse et al. . |
| 5,800,458 | 9/1998 | Wingrove . |

OTHER PUBLICATIONS

Glenn F. Pierce et al, "Pharmacologic Enhancement of Wound Healing", Annu. Rev. Med. 1995, 46:467–81, 1995.

CA Salzberg et al, The effects of non–thermal pulsed electromagnetic energy on wound healing of pressure ulcers in spinal cord–injured patients: a randomized, double–blind study, Ostomy Wound Management, 41(3): 42–4, 46, 48 passim, 1995 Abstract only.

PULSED ELECTROMAGNETIC ENERGY TREATMENT APPARATUS AND METHOD

This application claims the benefit of provisional application no. 60/071,396, filed Jan. 15, 1998.

TECHNICAL FIELD OF THE INVENTION

This invention relates to electromechanical devices and methods for therapeutically treating human body tissue, and more particularly to a device for and a method of stimulating cell proliferation and related molecular events using high frequency pulsed electromagnetic energy.

BACKGROUND OF THE INVENTION

The present invention is an important advancement in the fields of endogenous pharmacotherapeutics, electromagnetic medicine, wound physiology and treatment, and regulation of the cell cycle, and has specific application in the area of wound healing, and in particular, the healing of chronic wounds, such as pressure ulcers, diabetic ulcers and venous stasis ulcers. Prior to discussing the present invention in detail, it is helpful to understand the specific mechanisms of wound healing, the immediate need for wound healing therapies, and the current state of the art.

While the specific mechanisms of action have not been fully determined, research over the past several years has substantially increased understanding of the nature of wound healing and the elegant cascade of signaling events necessary for the initiation of cell growth and migration and tissue regeneration, which collectively constitute the wound healing process. Importantly, numerous biochemical mediators of cell migration patterns and cell-cell/cell-extracellular matrix interactions involved in the reformation of tissue/organ systems have been identified.

There are distinct phases associated with the process of wound healing. In the inflammatory phase, platelets aggregate to deposit granules, which promote fibrin deposition, and stimulate the release of growth factors. Leukocytes migrate to the wound site and begin to digest and transport debris away from the wound. It is also during the inflammatory phase that monocytes are converted to macrophages, which release growth factors for stimulating angiogenesis and the production of fibroblasts. Next, in the proliferative phase, granulation tissue forms and epithelialization begins. Fibroblasts, key cell types in this phase, proliferate and synthesize collagen to fill the wound and provide a strong matrix on which epithelial cells grow. As collagen is produced by fibroblasts, vascularization extends from nearby vessels to supply nutrients to the regenerating tissue. The red loops of blood vessels give the wound a granular appearance, thus the term granulating. Epithelialization involves the migration of epithelial cells from the wound surfaces to seal the wound. Epithelial cells are driven by the need to contact cells of like type and are guided by a network of fibrin strands which function as a grid over which these cells migrate. Contractile cells called myofibroblasts appear in wounds and aid in wound closure. These cells exhibit collagen synthesis and contractility, and are common in granulating wounds. In the final phase of wound healing, the differentiation or tissue remodeling phase, collagen in the scar undergoes repeated degradation and resynthesis. It is during this phase that the tensile strength of the newly formed skin increases.

Clearly, growth factors are important messengers in coordinating this complex orchestration of cellular events. Today, growth factors refer to an expanding class of molecules, sometimes with specificity for certain types of cells, that can have either pro-proliferative or antiproliferative/differentiation effects, depending upon the specific circumstances. Their immediate molecular targets are specific members in the superfamily of receptor tyrosine kinases. Relatively little is known about the regulation of growth factor activity, but spatial and temporal gradients of growth factor and receptor expression are evident, and expression of a given growth factor or its receptors can be induced by other growth factors, suggesting that sequences of growth factor-mediated messages networked across cell types and integrated with other signaling cascades are central to tissue/organ development, maintenance and healing processes.

Thus, the recent realization that growth factors can serve as paracrine, autocrine, juxtacrine and intracrine (which refers to actions of growth factors within a cell) signals to regulate proliferation, migration, and interaction of cells critical to wound healing is important to understanding and developing wound treatments. For example, central to tissue/organ repair and remodeling is the critical revascularization of damaged tissue. Vascular endothelial growth factor (VEGF) is a recently discovered agent that promotes proliferation and migration of endothelial cells. Stimulating the expression of VEGF receptors in endothelial cell precursors allows those cells to respond to VEGF secreted from other cells or to VEGF acting via autocrine/intracrine mechanisms. Stimulating the release of VEGF from fibroblasts and/or other cell types (or stimulating VEGF production in endothelial cells) promotes mitotic and/or migratory activity of endothelial cells. Also critical to tissue repair is establishment of the extracellular scaffold to support cell migration and/or proliferation. Stimulating the release of agents such as fibroblast growth factors (FGF) from any of a number of cell types promotes proliferation and migration of fibroblasts, which are involved in production of extracellular matrix materials such as collagen. Moreover, stimulating FGF receptor production in fibroblasts capable of recognizing paracrine, autocrine, or intracrine FGF also plays a role in stimulating fibroblast activity and the production of extracellular matrix. Other agents implicated in tissue repair include insulin-like, platelet, transforming, and epidermal growth factors. Those molecules and their receptors are the likely molecular substrates for tissue repair. Endothelial cells, fibroblasts and keratinocytes, among others, are the cell types whose activity is critical to tissue repair and represent the likely cellular targets for these growth factors and related molecules associated with the healing of pressure sores.

It is also well known that regulatory signals normally found in the repair of acute wounds are not present in chronic wounds such as pressure ulcers and venous stasis ulcers. For example, chronic wounds frequently have poorly vascularized, thick fibrotic scar tissue surrounding the wound bed, are characterized by keratinocytes incapable of proliferation and migration, and have few active fibroblasts. These occurrences are clearly indicative of defects in growth factor signaling.

With the understanding that defects in growth factor signaling contribute to the development and/or persistence of chronic wounds, it is logical to conclude that reinstitution or normalization of that signaling would promote wound healing. Growth factors have been considered candidate therapeutics for wound healing because they are synthesized by and stimulate cells required for tissue repair, they are deficient in chronic wounds, and there is some evidence that pharmacological application enhances wound repair in a variety of animal models of dermal incisional and excisional repair.

However, clinical studies have been disappointing and some experts have suggested that an alternative to single growth factors as therapeutic agents is the utilization of growth factors in combination to elicit synergistic clinical efficacy. This lack of therapeutic efficacy may be in part because wound healing is a complex programmed sequence of cellular and molecular events, including macrophage activation during inflammation, cell migration, angiogenesis, provisional matrix synthesis, synthesis of collagen by fibroblasts, and reepithelialization. Current pharmaceutical approaches do not fully mimic the necessary spatial and temporal patterns of growth factor activity needed to promote wound healing. Overall, the complexity and variability of clinical wounds have limited pharmacological approaches to accelerate wound healing, leaving dressings and nonpharmacological ancillary modalities to dominate the market associated with wound management.

A treatment regimen involving application of outside or exogenous growth factors and other medicinal agents to the wound site is but one approach that has been pursued in the treatment of wound healing. Various medical treatment devices utilizing physical energy emissions to stimulate wound healing have also been developed over the past 40–50 years. Most of these devices involve the use of applied electrical currents to stimulate growth in bone or soft tissue. Another major group of devices utilizes the passage of electrical currents through coils of wire to create magnetic fields which are applied either by placing the coil in proximity to the human body or by wrapping the coils around the body or limb. Finally, a number of devices have been developed which utilize an antenna or tank circuit to apply Radio Frequency (RF) electromagnetic energy to the body for the purposes of medical treatment. Most devices in this latter category utilize continuous energy output to create thermal energy within the tissue. However, a subcategory of these devices utilize pulsed electromagnetic energy output to theoretically stimulate tissue without inducing a thermal response, although this has never been completely proven to occur using existing devices. There have been observations that some of these devices appear to stimulate or accelerate the wound healing process but there has been no sound, scientific data offered to explain how such devices might work at the cellular or molecular levels.

One area in which health care professionals and insurance providers are demanding improved treatment regimes is in the treatment of chronic wounds. In the United States, where wound care constitutes less than 1% of aggregate health care dollars, treating and managing pressure ulcers requires an inordinate amount of material, human resources, time and money. The costs associated with managing just one type of chronic wound alone, pressure ulcers, are extraordinary.

To enhance quality and decrease the cost of health care, the Agency for Health Care Policy and Research (AHCPR) was established by the U.S. government in 1989. That agency published Clinical Practice Guidelines for both prevention and treatment of pressure ulcers in 1992 and 1994, respectively. The release of these guidelines substantially increased biomedical awareness of patients with pressure ulcers, including the elderly and those afflicted with various spinal and neurological disorders. Importantly, the Health Care Financing Administration (HCFA) utilizes these guidelines to create medical policy and reimbursement criteria. Electrotherapeutic modalities are the only type of adjunctive therapy recommended in the AHCPR Clinical Practice Guideline and supported by the Nation Pressure Ulcer Advisory Panel.

Electrotherapy includes various means for applying an electric or electromagnetic field to a wound area to facilitate growth and proliferation of new tissue, i.e., healing. Application of external electrical and electromagnetic fields is now an increasingly standard therapy for the treatment of nonunion bone fractures, but these devices have seen limited use in other areas of healing.

Clinical research has shown that treatment with electrical stimulation or electromagnetic fields can enhance the healing rate of pressure ulcers unresponsive to conventional therapy. For example, pulsed electrical stimulation has been shown to enhance the healing rate of decubitus ulcers. This therapeutic approach stems from observations for nearly 60 years that electric potentials over wounds are negative until healed, and the related hypothesis that living tissues possess direct current surface potentials that regulate the proliferative phase of healing and that healing can be induced by negative electrical potential. Unfortunately, this has led to unsubstantiated claims that electrical stimulation cures a wide variety of health problems, thereby alienating the medical profession. Though this idea is now archaic and simplistic in view of scientific studies of the cellular correlates of wound healing, the evidence suggests that electrical fields accelerate wound healing. While few well designed experiments concerning cellular mechanisms have been conducted, some published reports indicate that electrical stimulation activates macrophages and increases cell proliferation, collagen synthesis and the expression of fibroblast receptors for transforming growth factor-beta.

Treatment devices emitting magnetic and/or electromagnetic energy offer significant advantages over other types of electrical stimulators because magnetic and electromagnetic energy can be applied externally through clothing and wound dressings, thereby rendering such treatments completely non-invasive. Moreover, published reports of double blind placebo-controlled clinical trials utilizing a RF transmission device (Diapulse) suggest that this ancillary treatment device significantly reduces wound healing time for chronic pressure ulcers as well as for surgical wounds. Studies using Dermagen, a magnetic device manufactured in Europe which produces a low frequency magnetic field, have demonstrated significant augmentation of healing of venous stasis ulcers. Additionally, it has been shown that 50% fewer patients treated with electromagnetic energy develop reoccurring pressure ulcers, compared to control patients, suggesting that electromagnetic energy treatments impart some resistance to the reoccurrence of chronic wounds, such as pressure ulcers. Electromagnetic energy may also be useful as a preventative strategy. Perhaps most important from a practical clinical perspective, an actuarial analysis of the effects of electromagnetic energy on the treatment of pressure ulcers show that this treatment, by reducing healing time by an average of 50%, results in significant reductions in the costs associated with wound management.

One category of prior art magnetic/electromagnetic treatment devices utilizes the passage of electrical currents through coils of wire to create magnetic fields. The frequency of the electrical impulses is relatively low, typically in the low frequency or audio range. Other devices, which utilize electrical stimulation between electrodes, represent a substantially different approach to medical treatment from the present invention for the primary reason that such an approach is invasive and more difficult to use and involves the attachment of electrodes at or near the wound site.

Another category of prior art electromagnetic treatment apparatus includes high frequency, high power devices utilizing pulsed electromagnetic energy output to stimulate tissue without inducing a thermal response. This category of devices is represented by the inventions disclosed in the following U.S. patents: Milinowski, U.S. Pat. Nos. 3,043, 310 and 3,181,535; Kendall U.S. Pat. No. 3,543,762; Pearo U.S. Pat. No. 3,670,737; and most recently Rauch et. al., U.S. Pat. No. 5,584,863. Those earlier inventions first described and defined the principle and operation of pulsed, high frequency energy output devices and/or systems.

While numerous high frequency devices using pulsed electromagnetic energy to stimulate tissue growth have been developed, none have effectively addressed the needs of patients and health care providers. A recent attempt, as described in U.S. Pat. No. 5,584,863, is a pulsed radio frequency electrotherapeutic system having a pulse generator and an athermapeutic applicator head. The generator includes a power supply electrically connected to a remote current source by a cord, an exciter for generating pulsed signals of a selectable megahertz frequency, and an amplifier for amplifying the pulsed signals. A system controller having manually operable dials is provided for controlling pulse width duration, pulse burst repetition rate and power amplitude of the pulsed signals generated by the exciter. The amplitude of the signals outputted from the amplifier are compared with a reference value using a standing wave ratio (SWR) detector circuit, which in turn outputs power and impedance compensated signals to the applicator and produces a ratio signal that is delivered to the controller for adjusting the amplitude and phase of the signals generated by the exciter. The applicator, which includes a pair of spaced capacitor plates, a magnetic coil wound in a plane parallel to and electrically connected to the plates, and an RF shield, induces the received compensated signals into the tissue to be treated. Reactance and power level of the output of the applicator are manually controlled using an external tuning means connected to one of the capacitors. The device disclosed in U.S. Pat. No. 5,584,863 has high power requirements, requires numerous manual adjustments for effective operation, incorporates only a single applicator, fails to ensure constant, known and replicable treatment dosage outputs, and provides no confirmation that the applicator is properly located during treatment.

While the various and several prior art inventions, as described in the above referenced patents, produce electrical, magnetic or electromagnetic fields for treatment of tissue, virtually none of the prior art describes any credible cellular or physiological or molecular processes by which such energy fields specifically alter, induce or otherwise make happen an increase in cell growth, proliferation or density.

Additionally, none of the previous high frequency, high power devices utilizing pulsed electromagnetic energy output adequately addresses such practical design concerns as ease of use, simultaneous treatment of multiple wound sites on the same patient, dosage measurement, monitored dosage control and/or dosage compliance.

It would be desirable therefore to provide a method of and an apparatus for treating wounds with high frequency pulsed electromagnetic energy that is easy to implement, requiring minimal training in its proper and effective use, assures a constant, known and replicable dosage output, provides for simultaneous treatment of multiple wound sites, has low power requirements and is cost effective.

Citation of the above documents, devices and studies is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein.

SUMMARY OF THE INVENTION

In view of the foregoing limitations and shortcomings of the prior art, as well as other disadvantages not specifically mentioned above, it should be apparent that there still exists a need in the art for improved electromagnetic energy treatment apparatus and methods. It is therefore a primary object of the present invention to fulfill that need by providing a method of and apparatus for the treatment of chronic wounds using pulsed electromagnetic energy that is cost effective, easy to implement, and ensures proper treatment dosage delivery without the need for manual adjustment of power, pulse rate duration, pulse width duration, treatment time or reactance by the treatment provider.

More particularly, it is an object of this invention to provide an electromagnetic energy treatment apparatus with the ability to produce a constant, known and replicable treatment dosage output that is not adversely affected (i.e., does not negate consistent dosage or efficacy) by the proximity of the body of the patient (e.g., capacitance, inductance).

It is yet another object of this invention to provide an electromagnetic energy treatment apparatus wherein one or more wound sites may be simultaneously treated with different treatment dosages.

It is still another object of this invention to provide an electromagnetic energy treatment apparatus wherein the applicator is easily and accurately positioned directly on or adjacent to the wound site regardless of where the site is located on the patient.

Still another object of this invention is to provide an electromagnetic energy treatment apparatus wherein the applicator includes printed coils formed on one or more printed circuit boards, with the primary coil and secondary coil forming a matching network for effecting a highly efficient RF output. In other words, the applicator includes closely matched and tuned primary/secondary circuits, which greatly enhances efficiency by allowing the use of reduced power levels.

It is a yet further object of this invention to provide an electromagnetic energy treatment apparatus having the ability to affect living tissue by providing an accurate treatment dosage of 1 to 300 mw/cm$^2$ with very low input power requirements (i.e., an average power requirement in the range of less than three watts, and preferably less than about one watt).

It is a still further object of this invention to provide an electromagnetic energy treatment apparatus wherein treatment dosages are automatically monitored for safety by multiple sensing or detecting circuits and controlled by a field strength sensor.

It is a yet further object of this invention to provide an electromagnetic energy treatment apparatus that is small, portable, easy to use and safe to operate, with the apparatus automatically maintaining the appropriate treatment dosage and shutting down when certain conditions are present.

Briefly described, the present invention is an improved method of and apparatus for generating and administering treatment dosages of pulsed electromagnetic energy for wound healing applications. Specifically, the present invention generates and applies constant, known and replicable treatment dosages of electromagnetic energy of defined specifications to the human body for the purposes of inducing cell proliferation. In its preferred form, the present invention includes a pulsed electromagnetic energy generator, control means, including a power level controller responsive to signals from multiple sensing and control circuits, and one or more interchangeable treatment pad applicators. The generator, which can be battery-operated, is a low power, compact unit whose output is controlled by the multiple sensing and control circuits via the power level controller. The control circuits include integral sensing circuits for ensuring specified treatment dosage and the safety and effectiveness of the apparatus as a medical instrument, and one or more detectors located in or on each applicator for sensing energy output at the site of application and monitoring, with precision, the treatment dosage. Other circuits are included for disabling the apparatus when certain conditions, such as insufficient power, exist.

The generator of the present invention has multiple treatment ports to which one or more applicators are attached via cables to provide for the simultaneous treatment of one or more wound sites on the same patient. Preferably, the apparatus allows the applicators to operate independently and simultaneously at different treatment dosage levels. The applicators are treatment pads of various sizes comprising tuned tank circuits and a field strength sensor to allow for automatic control of the output specifications of the apparatus. Each applicator also has detectors for sensing proximity to the patient during the course of treatment and informing the patient if the applicator inadvertently moves from its intended treatment position.

The present invention has numerous advantages not found in existing electromagnetic energy treatment apparatus. First, the generator of the present invention is operationally efficient and has low power requirements, on the range of less than three watts of average power (preferably less than one watt). This allows the unit to be battery operated and greatly reduced in size, thereby rendering the apparatus portable and easy to use, as the small size facilitates transport and placement of the unit, with minimal disruption, in the patient's treatment area during use.

Another advantage of the present invention relates to its integration of multiple sensor and control circuits which, for the first time, ensures precise treatment dosage and provides confirmation that the applicator remains on the wound site during the entire course of treatment. In addition, these sensor and control circuits allow for unattended operation of the device during treatment, providing for a highly simplified means of treatment. The multiple monitoring and control circuits are separate and distinct, and include a fixed period treatment timer, forward and reflected power monitor circuits (one for each treatment port provided by the generator), an electromagnetic energy signal strength detector and controller circuit, and a treatment pad to patient proximity detector. Together, those control means guarantee that the correct treatment dosage reaches the patient.

Another advantage of the present invention not found in existing electromagnetic treatment devices is the multiple port generator for allowing the simultaneous use of multiple applicators. When using existing electromagnetic treatment devices, caregivers are limited to the treatment of just one wound site per each time interval of unit use. Because many pressure sore patients have two or more wounds, the present invention greatly reduces treatment time and expense since multiple wounds can be treated at once. Preferably, each treatment applicator is selected to operate simultaneously at a different treatment dosage level to accommodate multiple wound sites.

Each treatment applicator of the present invention also includes novel elements which overcome several major deficiencies in previous designs. Existing applicators are typically large volume, rigid extensions of the power sources. The applicator of the present invention is substantially reduced in size, bulk and power requirements. This is possible, in part, due to the utilization of low power and the increased operational efficiency of the generator and applicator itself. Preferably, each applicator is thin, flexible and constructed in any of a wide variety of shapes and sizes to accommodate various wound sites. In one embodiment, the treatment pad is configured as a rectangle with dimensions of approximately 10 inches by 5 inches and a nominal thickness of less than ½ inch. Each applicator is a flexible pad comprising one or more etched copper printed circuits laminated between insulating sheets of flexible material having high dielectric properties. The two circuits operate as an impedance matching transformer. Sensing units, including an electromagnetic signal strength detector and an applicator-to-patient proximity detector, are incorporated in each applicator and are in communication with the power level controller to provide for direct monitoring of the electromagnetic energy field and precise control of the treatment dosage. By modifying the topology of the etched printed circuit inductor portion of the LC circuit and then correspondingly adjusting the capacitance value of the capacitor to retune the LC circuit to resonance, the applicator can be constructed in a variety of shapes and sizes to best match the wound size and area on the patient. Moreover, the tank circuit in the applicator is pre-tuned, thereby eliminating the need to manually tune the circuit as it comes into close proximity with the human body or other objects. Given its nominal thickness and increased flexibility, the applicator can be placed over, under or around a bandaged wound site.

Other novel and unique features of the applicator include the following. Existing electromagnetic energy devices do not include mechanisms for delivering precise and replicable treatment dosages to the patient. Although previous designs may have specified that the applicator be tuned to resonance or may have included a mechanism for matching the generator and the applicator in order to minimize SWR, there has been no way to ensure that accurate treatment dosage was being delivered through the coils located in the applicator and beyond, to the surface of the patient's wound site. In the present invention, a signal detector, such as a germanium diode signal detector, is included as part of the applicator for measuring the energy emission from the applicator and supplying a feedback signal to the RF amplifier for controlling energy output. The actual electromagnetic energy field, or treatment dosage, that is transmitted from each applicator is measured directly by embedding the RF signal strength detector inside of the applicator. The signal level from the detector is sent to the power level controller, where it is used as a feedback-control signal to control the output of the RF amplifier of the generator. This direct approach to measuring the actual radiated electromagnetic energy field is a much more precise way to measure the treatment dosage, rather than by indirectly measuring the SWR of the transmitted RF signal. If, at any time, the detector measures a radiated energy output level above or below preset levels, an indicator, such as a "service required" lamp or alarm, audibly, visually or otherwise informs the health care provider and patient of the occurrence and the power level controller switches off the RF amplifier. The forward and reflected power measuring circuits are used to turn the unit off only if either circuit exceeds preset limits. In this manner, the present invention monitors energy emissions from each applicator and ensures that the treatment dosage delivered through each applicator is precise.

The applicator of the present invention is thin and need not be suspended on a mechanical arm, as required by some existing applicators. Because of the unique configuration of the present invention, a correct treatment dosage is easily and effectively delivered to the patient.

The present invention further includes a method of effectively treating chronic wounds such as pressure ulcers involving the precise induction of specific biochemical events associated with cell proliferation. In accordance with the present invention, an electromagnetic field of specified strength and duration is used to stimulate cellular growth and proliferation, membrane ionic flux, growth factor expression, release and functional enhancement, and reductions in cell doubling time. Electromagnetic energy fields are utilized to stimulate and accelerate cell growth and proliferation upon certain types of cells known to be critical to the wound healing process, including fibroblasts and epithelial cells. Electromagnetic stimuli induce cell proliferation by reducing the $G_0$ and/or $G_1$ phases of the cell cycle, by stimulating the genetic expression, release and functional enhancement of growth factors, and by inducing the flux of ions across cellular membranes. Therefore, the present invention acts as a mitogen and/or a positive modifier of cellular mitogenic activity. This mitogenic effect results in growth factor stimulation, expression and release, both intra-and extracellularly. A key component of the present method is the specific enhanced actions of fibroblast growth factors.

It is important to note that the present method, which utilizes electromagnetic energy as a stimulus for inducing cell proliferation through mechanisms regulating decreases in cell cycle time, is independent of the particular source of the energy emission or the design of the energy source. The term electromagnetic energy includes effects from its magnetic energy and/or electrical energy components.

The present method utilizes electromagnetic energy as a mitogenic stimulus to reduce cell cycle time through the expression, synthesis and enhanced activity of growth factors, thereby increasing the overall rate of growth and proliferation in various biological cell types, including those found in epithelial, muscle, connective and neuronal tissues. Energy waves which are primarily defined as Radio Wave frequencies are used to induce biological cell proliferation in vitro under laboratory conditions and in vivo under clinical conditions in intact living organisms. In the electromagnetic spectrum, those frequencies range from 1000 Hertz to 1000 Megahertz, and therefore also include a portion of the audio frequencies (at the lower end) and range through ultra high frequencies (UHF). The present method delivers an electromagnetic treatment energy of 1 to 300 milliwatts per $cm^2$ to living tissues (in vivo or in vitro). Because it is a specific cellular mitogen, the present method reduces cell cycle time through the induction of specific cellular mechanisms which reduce the duration of the separate and/or combined $G_0$ and $G_1$ phases of the cell cycle. Specific mitogenic physical energy signals are provided that induce cell growth and proliferation in part through the induction of ion flux across cellular membranes and subsequent cellular signaling events, including the expression, synthesis and enhanced activity growth factors, especially fibroblast growth factors. An electromagnetic energy stimulus is utilized to activate intracellular and intercellular mechanisms associated with the genetic expression, synthesis and release of biological molecules necessary to regulate cell cycle time.

Because the present method is based upon discoveries pertaining to the effects of specific doses of electromagnetic energy on in vivo and in vitro cells and tissues, the present method offers the significant advantage of fixed power output, pulse rate and pulse width to specifically increase cell growth and proliferation in distinct cell types found in soft tissue, connective tissue, and neuronal cells. Treatments applied using the present method are characterized by specific optimal dosages of pulsed electromagnetic energy to induce cell proliferation of specific cell types. The present method allows utilization of a fixed pulse rate, a fixed pulse width and a fixed energy field strength to define and produce the optimal energy specifications to be used to stimulate specific cell types related to specific medical indications or specific treatment regimens. It also provides for the creation and application of specific dosages and treatment regimens which are required for specific medical indications. Further, the present method can also be implemented to treat wounds other than ulcers, including burns, physical rehabilitation, and neuronal injury.

The present invention has immediate commercial market potential in the treatment of chronic wounds. Beyond that immediate market, the present invention may also be utilized in other treatment areas where increasing the rate of growth and proliferation of human or other living cells is essential, including the treatment of burns and surgically implanted skin or soft tissue grafts, rehabilitation medicine, post surgical repair, and neuronal/brain/spinal injury repair and regeneration. In addition to the medical treatment of soft tissue, the present method has applications in the field of laboratory growth/manufacturing of skin grafts to be sold and used in various surgical settings, veterinary medicine and related fields.

These and further and other objects and features of the invention are apparent in the disclosure, which includes the above and ongoing written specification, with the drawings.

DETAILED DESCRIPTION OF THE INVENTION

Figure 1:
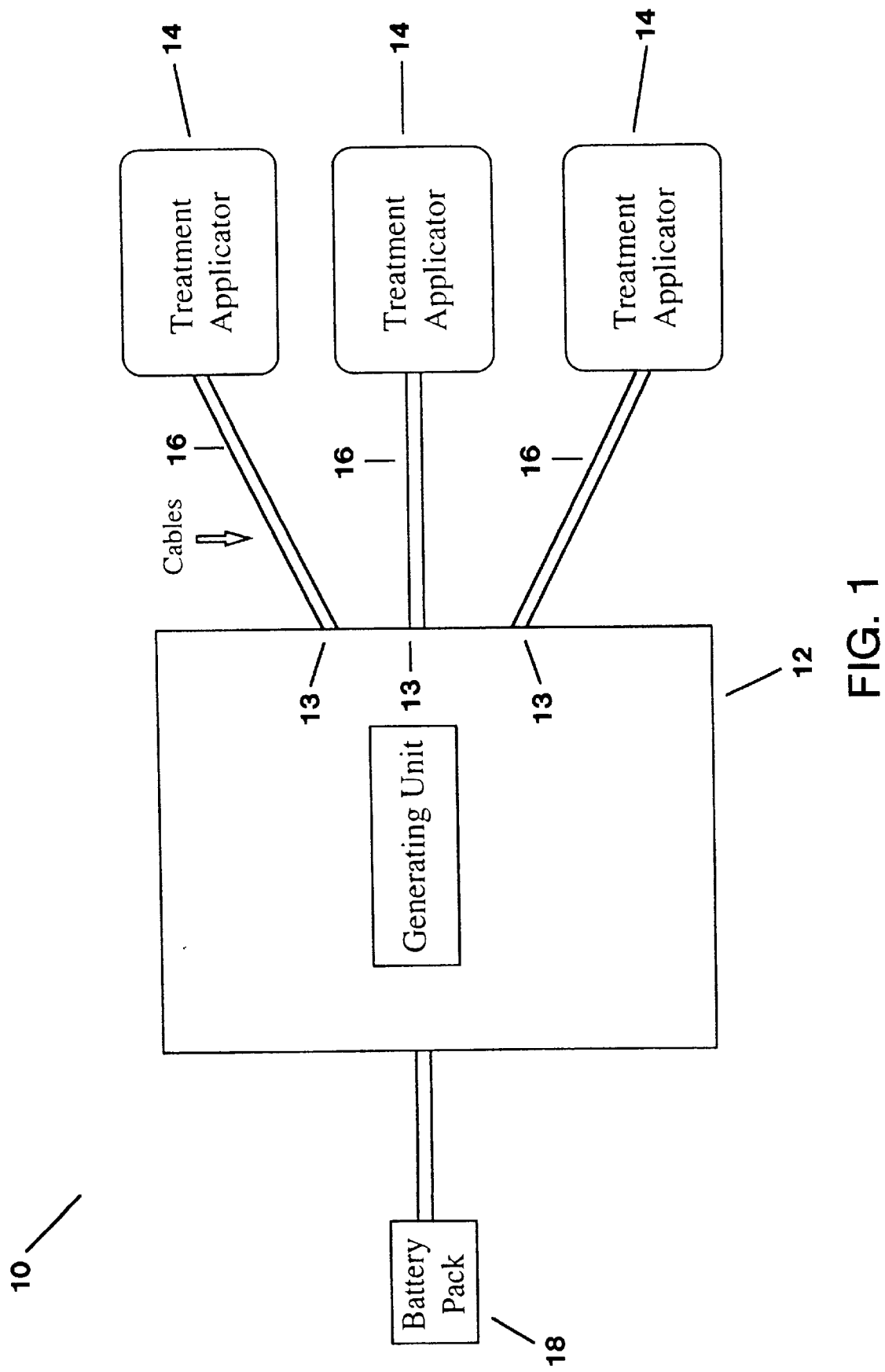
FIG. 1 is a block diagram of the generating unit and applicator components of the treatment apparatus of present invention.

Referring now to the drawings, where like elements are designated by like reference numerals throughout, FIG. 1 shows an apparatus 10, more fully described below, for treating wounds with electromagnetic energy. Apparatus 10 includes an electromagnetic energy generating unit 12 with multiple ports 13, and multiple applicators 14 connected to unit 12 by coaxial cables 16. A power source 18, such as a battery pack, is provided for delivering a current input to unit 12. While shown in FIG. 1 as a remote unit, battery pack 18 can be incorporated as part of unit 12. Since the present invention has low power requirements, the power source can be one capable of providing an average power input of less than three watts.

Figure 2:
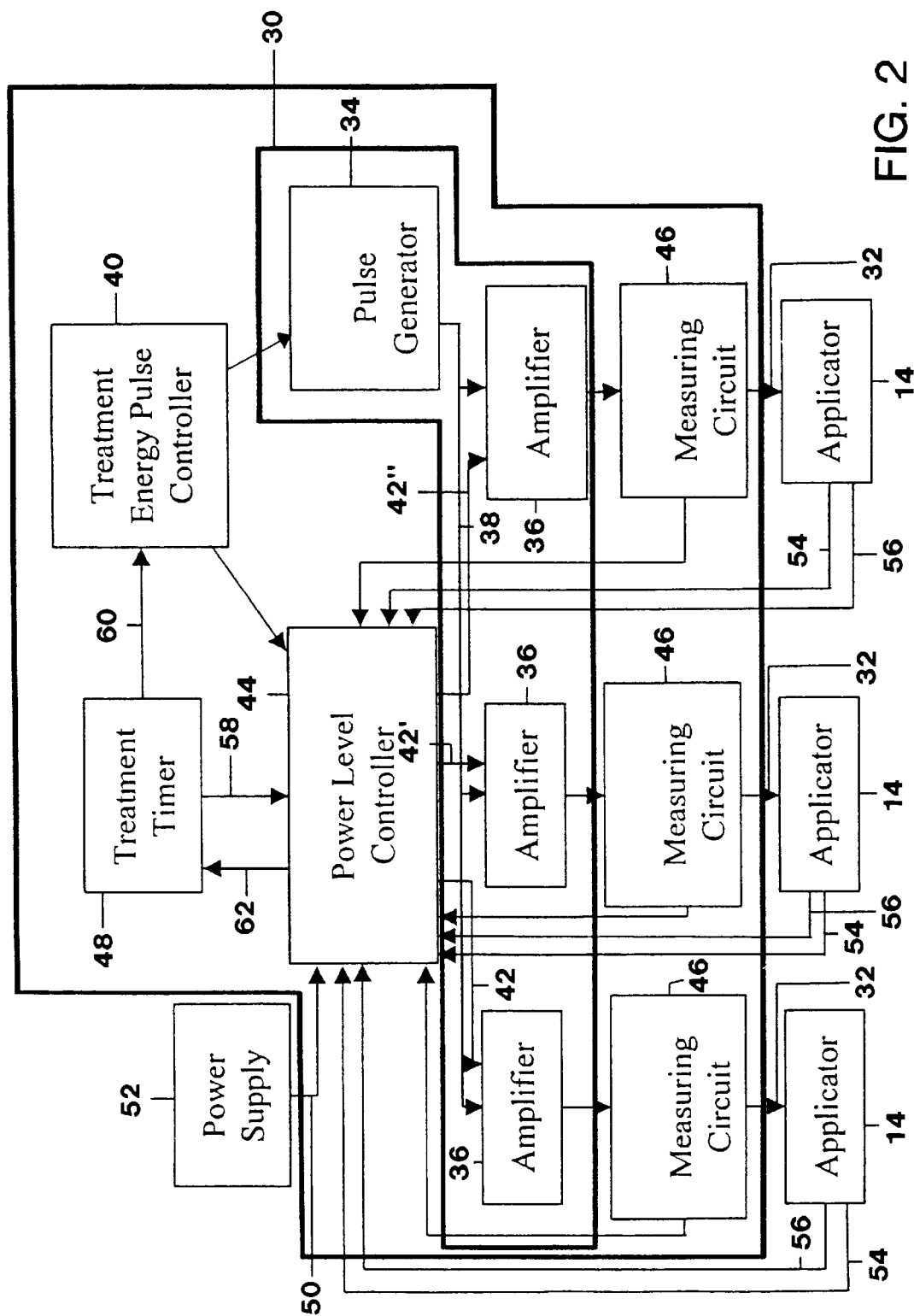
FIG. 2 is a detailed block diagram of the apparatus of FIG. 1.

Referring to the block diagram of FIG. 2, unit 12 includes a generator 30 for producing a pulsed high frequency signal output 32 and at least one applicator 14 having output 32 as its input. Generator 30 includes a pulse generator 34 and one or more amplifiers 36 having as their inputs a pulsed signal output 38 from the pulse generator 34. The number of amplifiers 14 is preferably equal to the number of treatment ports, such that each applicator 14 has an input from a single amplifier 36.

Treatment energy pulse controller 40 is connected to pulse generator 34 for automatically controlling characteristics of output 38 such as pulse rate and pulse width. Output 38 is delivered to amplifiers 36, each of which is individually responsive to signals 42, 42i, 42ii generated by power level controller 44. Control signals 42, 42i, 42ii from the power level controller 44 reflect feedback information 54 from the field strength detector positioned on each applicator 14. One or more control circuits, including the forward and reflected power measuring circuits 46, the treatment timer 48 and the treatment energy pulse controller 40, detect abnormal conditions and disable operation when appropriate. The power level controller 44 is also responsive to control signals 50 generated by control circuitry in the power supply assembly 52 and control signals 56 received from one or more proximity detectors located on the applicators 14. Treatment timer 48, which delivers activation signals 58, 60 to the power level controller 44 and the treatment energy pulse controller 40, respectively, for instituting the treatment process over a predetermined period of time, is also responsive to shut down signals 62 from the power level controller 44 for disabling the apparatus 10 when certain conditions are detected.

The embodiment of the unit shown in FIGS. 1 and 2 has three treatment ports 13 for simultaneously and independently delivering different output signals 32 to three separate applicators 14. It should be understood that the number of ports 13, amplifiers 36 and measuring circuits 46 may be varied without departing from the scope of the present invention.

The apparatus shown in FIG. 2 operates as follows. Signals 58, 60 from treatment timer 48 enable the power level controller 44 and the treatment energy pulse controller 40, respectively, thereby enabling the pulse generator 34 to produce pulsed signal output 38. Controller 44 automatically controls specific characteristics of the pulsed signal output 38 produced by generator 38 and received by amplifiers 36, including pulse rate, pulse width and pulse power level. The pulsed signal output 38 is thus amplified in accordance with instructions received from the power level controller 44, and specific outputs 32 are produced. Each of the outputs 32 may be different, depending on the specific instructions delivered to each amplifier 36 by controller 44. Outputs 32 from each amplifier 36 are evaluated by forward and reflected power measuring circuits 46 and delivered to applicators 14 which, in turn, use the output to apply a treatment dosage of electromagnetic energy to the patient.

The power level controller 44 individually instructs each amplifier 36 in accordance with specific information received from the field strength detectors located on the applicators 14. As described in greater detail below, power level controller 44, in conjunction with multiple control circuits, also provides for automatic disablement of the apparatus when treatment is complete, when treatment dosages are at unacceptable levels, or when inadequate power is being delivered to the apparatus. For multiple applicator embodiments, unit 12 may include a single controller 44 with multiple circuits, each dedicated to a single amplifier 36, for controlling multiple applicators 14, or multiple separate and distinct controllers 44, each having a single circuit for controlling a single applicator 14.

Figure 3:
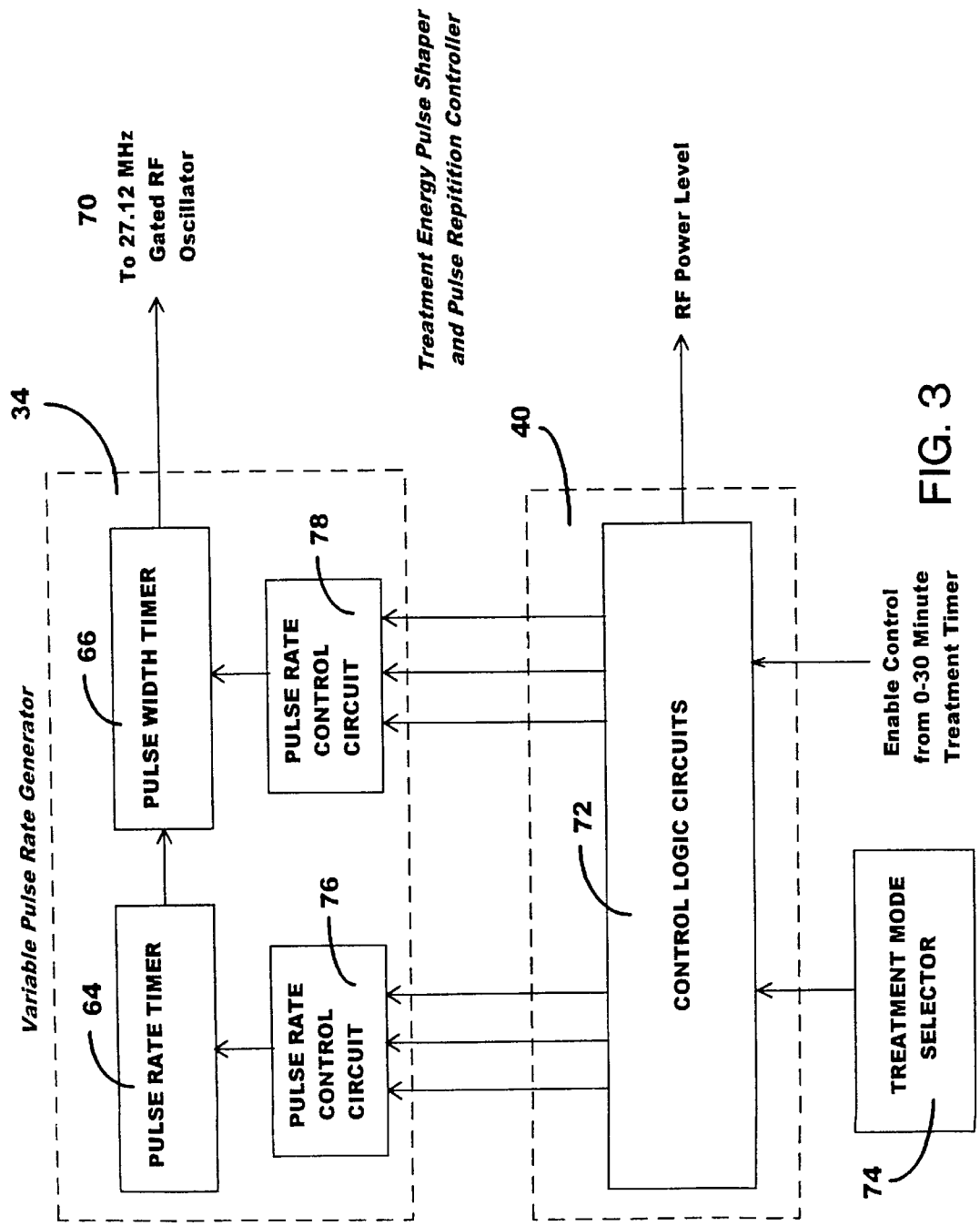
FIG. 3 is a block diagram of the pulse rate generator and treatment energy pulse controller located in the generating unit of FIG. 1.

FIG. 3 is a block diagram of the pulse rate generator 34 and treatment energy pulse controller 40 shown in FIG. 2. Generator 34 includes three major subcircuits. The first subcircuit is a pulse rate timer 64 for generating a controlled frequency of occurrence of the pulse envelope. Timer 64 sets the period, or pulse rate, of treatment dosage. The output of timer 64 is sent to a second subcircuit, the pulse width timer 66, which produces a single consistently shaped pulse envelope. The output of timer 66 is then used as an enable pulse for the gated high frequency RF oscillator 70 of the pulse generator 34. Oscillator 70 generates electrical signals reflecting the characteristics defined by the enabling pulse. The generated electrical signal output 38 is then delivered to amplifiers 36 which increase the size or amplitude of the signals in response to instructions received from the power level controller 44.

For specific wound treatments, it has been demonstrated that maximum effectiveness results when the RF pulse rate, RF pulse width, and peak RF power level of the enable pulse are set at specific values. For example, the $ED_{50}$ dose for optimum stimulation of human and other mammalian fibroblasts is about 15 mw/cm$^2$ average RF power, with an $ED_{99}$ of about 32 mw/cm$^2$, while the $ED_{99}$ for epithelial cells is about 100 mw/cm$^2$. These dosages are based upon pulse envelopes with an optimum pulse duration of about 32 microseconds and a repetition rate of about 1,000 pulses per second. For example, in one embodiment particularly effective in treating pressure ulcers, timer 64 is set at between about 1,200–1,500 pulses per second, and timer 66 is set at between about 16–20 microseconds, giving an output of between about 30–40 mw/cm$^2$ average power. In another effective embodiment, timer 64 is set at between about 900–1,200 pulses per second, and timer 66 is set at between about 30–45 microseconds, giving an output of between about 30–65 mw/cm$^2$ average power. In another effective embodiment, timer 64 is set at between about 600–1,000 pulses per second, and timer 66 is set at between about 32–60 microseconds, giving an output of between about 30–100 mw/cm$^2$ average power. Other treatment profiles are possible and can be used without departing from the scope of the present invention.

Referring once again to FIG. 3, automatic control of operating parameters (e.g., pulse rate, pulse width, RF power level, treatment time, etc.) is managed by a treatment energy pulse shaper and pulse repetition controller circuit 40. Circuit 40 includes a custom control logic circuit 72 having numerous treatment profiles preset therein. A treatment mode selector control 74 permits the operator to quickly select one of the stored profiles. Pulse control circuit 76 receives the signal from circuit 72 reflecting the desired pulse rate for the selected profile and sets the pulse rate timer 64 accordingly. Similarly, width control circuit 78 receives the signal from circuit 72 reflecting the desired pulse width for the selected profile and sets the pulse width timer 66 accordingly. Further, an RF power level is selected by the control logic circuit 72 and an appropriate signal reflecting that selection is sent to the power level controller 44, shown in FIGS. 2 and 5.

The ability to easily select and automatically control operating parameters (e.g., pulse rate, pulse width, and RF power level) is a very important feature lacking in previous devices. By employing a control logic circuit 72, a plurality of treatment RF pulse profiles (combination of specific RF pulse rates, RF pulse widths, and RF power level) can be easily preset during assembly and manufacture.

Treatment mode selector control 74 is included to allow the operator to easily select the appropriate treatment profile. In one embodiment, control 74 is a rotory selector switch. Preferably, the positions are clearly labelled as to their function. In another embodiment, control 74 is a touch pad or series of depressible buttons or keys for electronically or otherwise inputting a selection. It is understood that any means for selecting one or more of a number of stored profiles is contemplated by the present invention. In preferred embodiments, the only operator control besides control 74 is the Start/Stop button 80 (FIG. 4).

In one embodiment of the present invention, the control logic circuit 72 is preset with a single treatment profile. In that embodiment, the actuating means (e.g., start/stop button 80) is all that is required to select and start treatment.

Where multiple applicators are used, the unit 12 is provided with multiple treatment selector controls 74, one for each applicator 14. It is possible, however, to combine those controls in a single structure (e,g., a touch pad).

Figure 4:
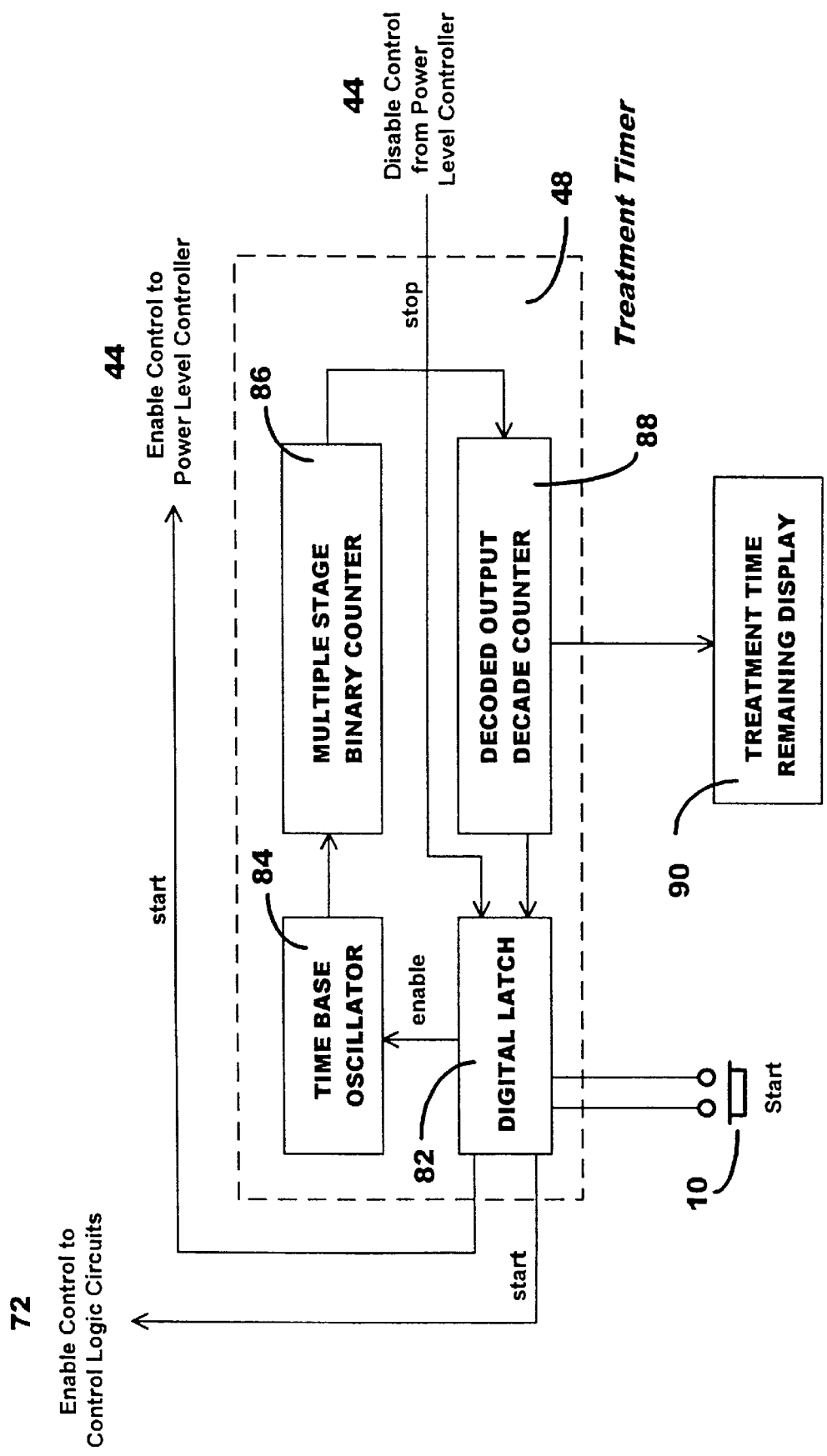
FIG. 4 is a block diagram of the treatment timer located in the generating of FIG. 1.

FIG. 4 is a block diagram of treatment timer 48. To regulate the amount of time, or treatment dosage, that a patient is receiving the applied pulsed RF energy, a digitally controlled treatment timer 48 is provided. The treatment timer 48 is started by pressing an actuator 80, such as a start/stop push-button, and is stopped by the operator by again pressing the actuator 80.

Pressing actuator 80 sets digital latch 82. Setting the digital latch 82 starts several actions. First, a signal is sent to the treatment energy pulse controller 40 to enable its operation. Second, a signal is sent to the power level controller 44 to enable its operation. Third, setting the digital latch 82 enables a time base oscillator 84. The output of oscillator 84 is sent to a multiple stage binary counter 86, which at its last output stage, produces an extended square wave pulse after a fixed period of time. This square wave pulse is then sent to a timer control 88, producing exclusive output signals. Timer counter 88 is preset to a predetermined treatment time, automatically controlled by logic circuit 72, or set by the operator using the treatment selector control 74. When the timer control 88 counts down to a value of zero, an end of treatment output pulse is initiated and this pulse is then used to reset the digital latch 82, disable the time base oscillator 84, and disable the control logic circuit 72. While the timer control 88 counts down, it is simultaneously sending signals which drive and correctly illuminate a treatment time display panel 90. The treatment timer 48 can also be stopped by a disable pulse received from the power level controller circuit 44. The disable signal is automatically generated when an operating deviation in the RF output circuitry is detected.

Figure 5:
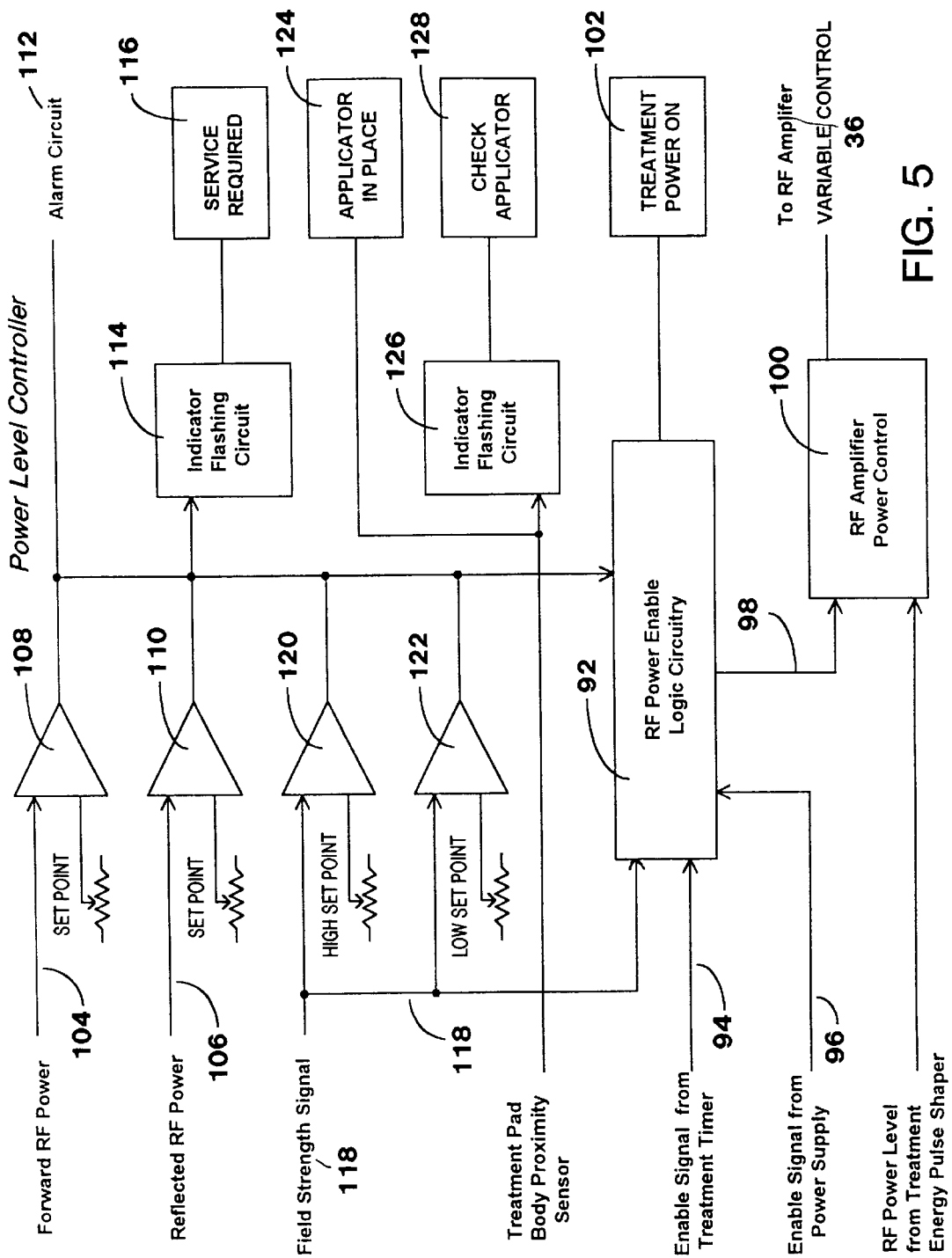
FIG. 5 is a block diagram of the power level controller located in the generating unit of FIG. 1.
Figure 6A:
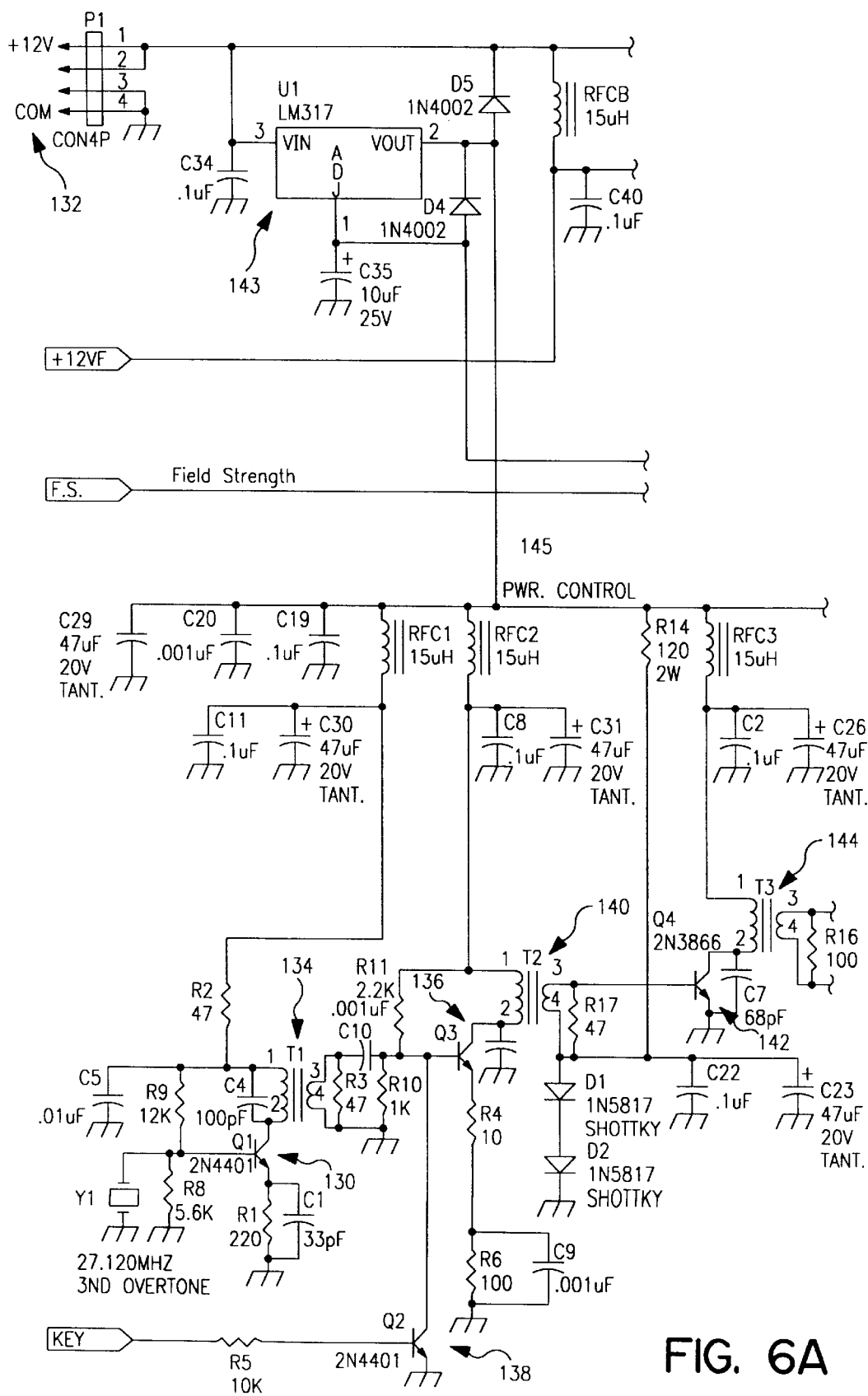
FIG. 6 is a schematic of one embodiment of the circuit for controlling the output of the pulse generator.
Figure 6B:
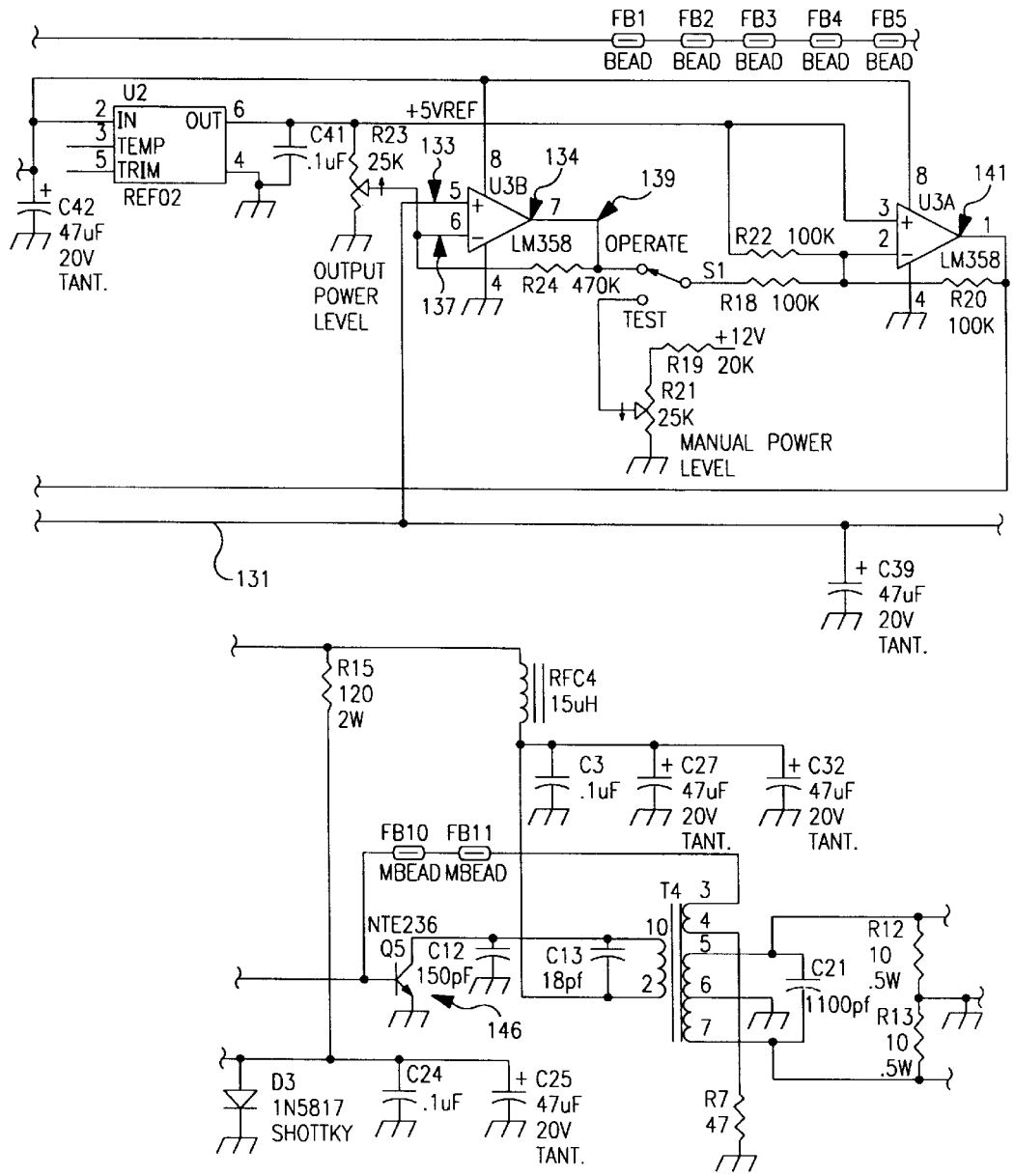
Figure 6C:
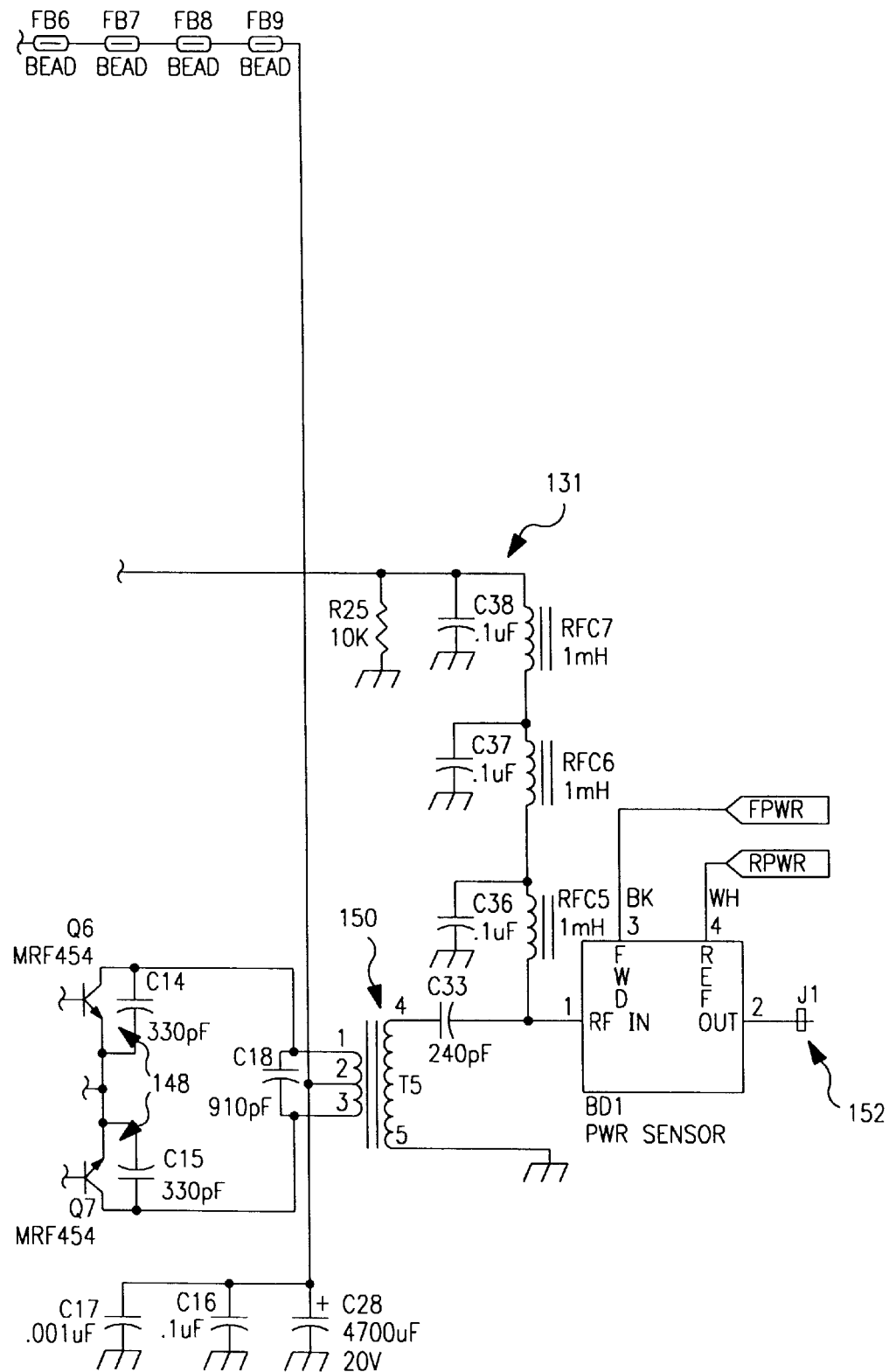

FIG. 5 is a block diagram of a power level controller 44 for incorporation in the present invention. The power level controller 44 is a multi-function circuit that can monitor and control the pulsed RF energy outputs to multiple applicators 14. Many of the sub-circuits shown in FIG. 5 are repeated for each treatment applicator. For the sake of clarity, FIG. 5 illustrates only one of these sub-circuits, and includes additional circuits that are common for basic treatment applicator operation. FIG. 6 completes the overall interconnections for operation, and illustrates multiple sub-circuits required for, as an example, three treatment applicators 14.

The controlling sub-circuit that permits pulsed RF energy to reach a treatment applicator 14 is the RF power enable circuit 92. Circuit 92 is activated by an enable signal 94 from the treatment timer 48 and an enable signal 96 from the isolated power supply control 52. When enabled, the RF power enable circuit 92 sends an RF power enable signal 98 to the RF amplifier power control 100. Circuit 100 controls the RF power level to the RF power amplifier 36. When RF power is being transmitted to the treatment applicator pad 14, the RF power enable circuit 92 switches on an indicator lamp 102.

Forward RF power signals 104 and reflected RF power signals 106 from measuring circuit 46 are delivered to voltage comparators 108 and 110, respectively. Voltage comparators 108 and 110 allow the setting of maximum forward and reflected power levels. If either of the measured power outputs is above/below its respective set-point level, a disable signal is sent to the RF power enable logic circuit 92, switching off RF power to one, a few or all low power RF amplifiers 36, switching off the treatment timer 48, and sending a signal to an optional alarm circuit 112. During a high forward or reflected power condition, indicator flashing circuit 114 is enabled which then starts flashing the single service required LED 116.

Figure 11:
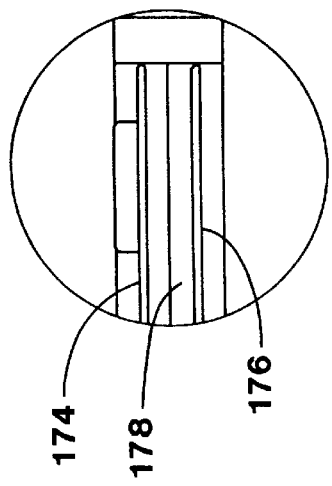
FIG. 11 is a cross-sectional detail A of the applicator of FIG. 10.

The actual RF energy that is transmitted from each treatment applicator 14 is measured by a detector located on the treatment applicator (FIG. 11). This field strength signal 118 is used to automatically regulate and control the RF output to the treatment applicator 14. Additionally, signal 118 is evaluated to determine if operation of the apparatus should be halted. Specifically, comparator 120 sets a maximum field strength level, and comparator 122 sets a minimum field strength level. If the measured field strength is outside these limits, a disable signal is sent to the RF power enable logic circuit 92, switching off RF power to all RF amplifiers 36, switching off the treatment timer 48, and sending a signal to an optional alarm circuit 112. During an out-of-range condition, indicator flashing circuit 114 is enable which then starts flashing the single service required LED.

When the treatment applicator 14 is in place, a body proximity sensor switch (FIG. 9) is closed, and the applicator in place LED 124 is illuminated. If this switch inadvertently opens, an indicator flashing circuit 126 is enabled and the check applicator LED 128 flashes.

FIG. 6 describes in more detail how one embodiment of the present invention operates. Initially, a crystal controlled oscillator 130 is stimulated following input of a DC supply voltage 132. The oscillator then generates a sine wave output 134 having a frequency of about 27.12 MHz to a preamplifier 136 controlled by an external switch 138 so that its output 140 consists of pulses of specific duration and repetition rate as controlled by the pulse rate generator and treatment energy pulse shaper and pulse repetition controller 40. The output of this stage of gain drives another amplification stage 142 which draws no current unless an input signal is present (Class C amplifier). This particular feature is an important improvement in that it is one of the features allowing for the use of a very low power amplifier to drive an effective output treatment RF signal. The output 144 of amplifier stage 142 then drives two additional power amplifiers 146, 148, also operating as Class C amplifiers. The Class C operation of additional power amplifiers 146, 148 also contributes to the ability to use low input power. The output 150 of the final amplifier is applied to the treatment applicator 14 via a coaxial cable connected to port 152.

FIG. 6 further shows one preferred circuit for adjusting the amplifier output. Field strength signal 131 is applied to one input 133 of comparator 135. The other input 137 of comparator 135 is a preset signal or a voltage from the controller. The output 139 of comparator 135 goes to opeational amplifier 141. The signal is then amplified further by voltage regulator 143. Voltage regulator 143 supplies DC power to the RF oscillator 130 and amplifier, thereby adjusting the output of the amplifier and, hence, the treatment dosage.

Figure 7:
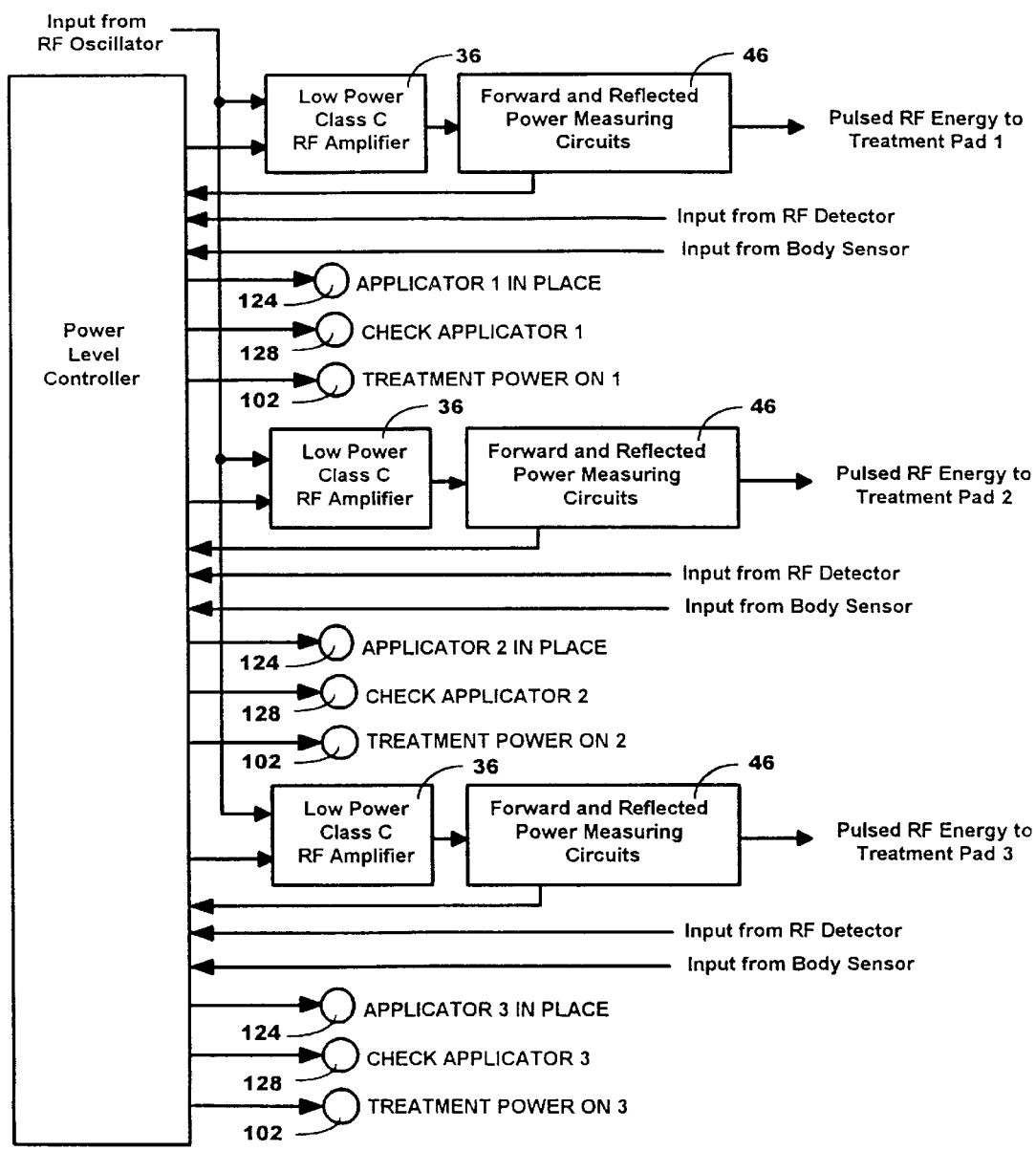
FIG. 7 is a block diagram of one embodiment of the generating unit of FIG. 1 having circuits for separately controlling multiple applicators.

FIG. 7 is a block diagram of an embodiment of the present apparatus 10 having multiple treatment applicators 14. As previously discussed, the power level controller 44 includes multitasking circuits that permit the addition and separate control of multiple treatment applicators 14. As shown in FIG. 7, the present invention allows for the concurrent treatment of multiple wound sites on a single patient where each wound site requires a different treatment profile.

Figure 9:
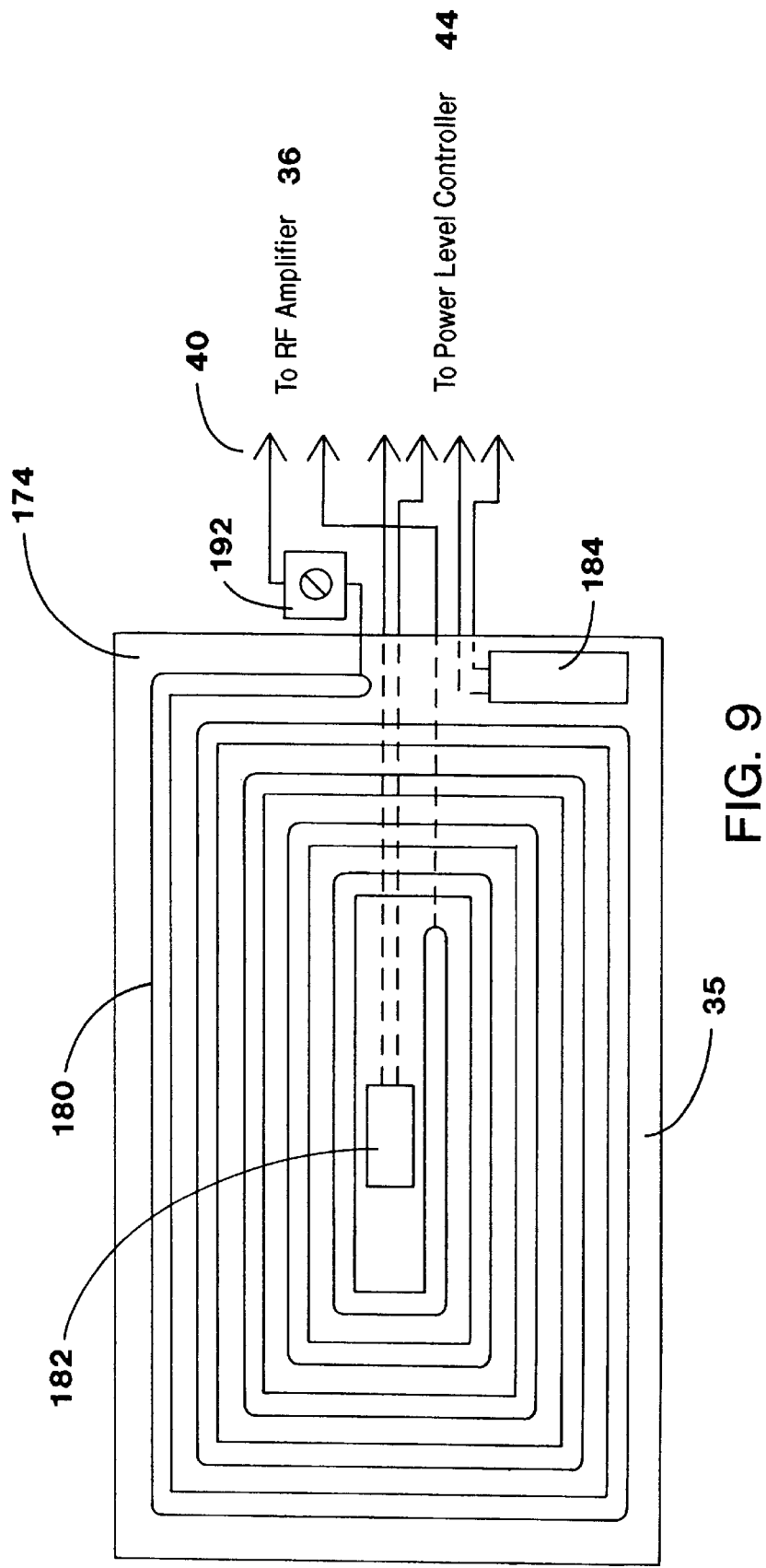
FIG. 9 is a plan view of one embodiment of the applicator of the apparatus of FIG. 1.
Figure 10:
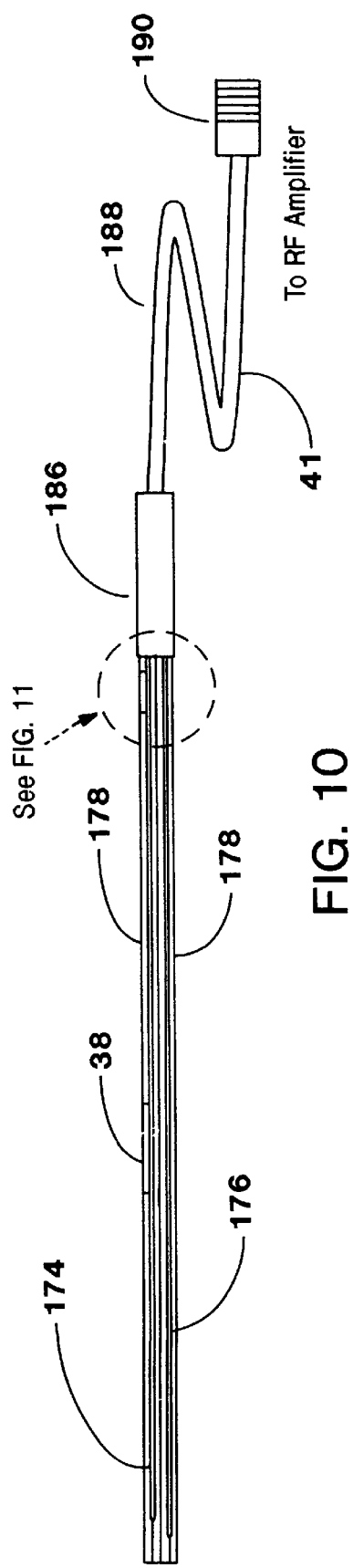
FIG. 10 is a front view of the applicator of FIG. 9.

FIG. 7 illustrates the embodiment of multiple sub-circuits that are required for, as an example, three treatment applicator pads. Each autonomous circuit incorporates separate low power class C RF amplifiers 36 and forward and reflected power measuring circuits 46. Separate indicator lamps 102, 124, 128 are provided for applicator in place 27, check applicator 28, and treatment power on 29. Separately controlled RF energy pulses, which are transmitted through the individual forward and reflected power measuring circuits 46 are connected to separate treatment applicators 14 via labeled flexible cables, each applicator 14 having its own detectors and sensors (FIGS. 9 and 10).

From each treatment applicator 14, separate signals from the detector and body proximity sensor are sent to individual control circuits in the power level controller 44 to independently monitor and control the RF output level radiating from each treatment applicator 14.

Each control circuit of the power level controller 44 is automatically activated when a treatment applicator 14 is connected to the electromagnetic energy output device. When a treatment applicator 14 is disconnected, or if its body proximity sensor is in an open circuit condition, the associated control circuit of the power level controller 44 is automatically deactivated.

Figure 8:
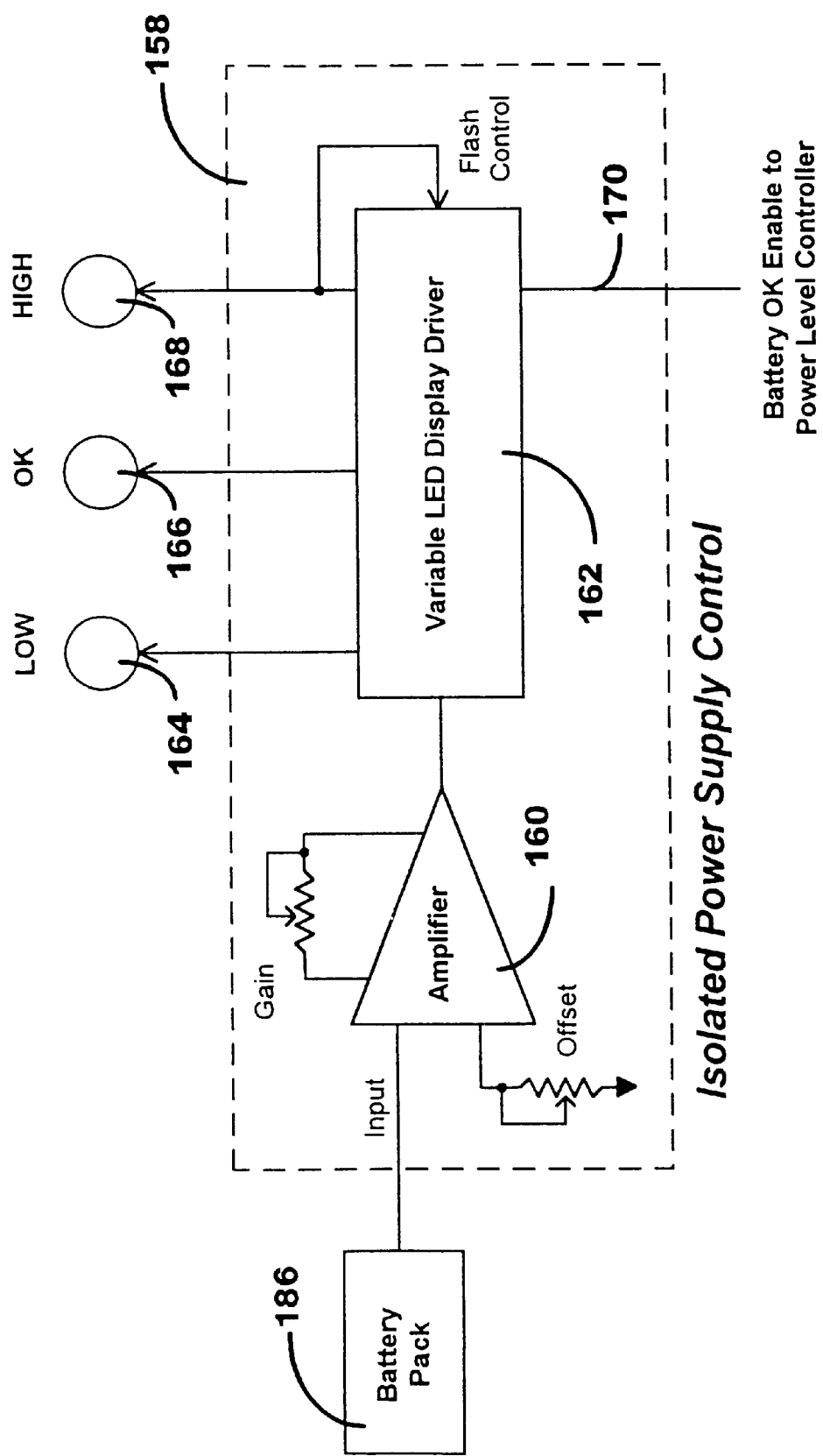
FIG. 8 is a block diagram of the isolated power supply assembly for the treatment apparatus of FIG. 1.

FIG. 8 is a block diagram of an isolated power supply assembly 52 of the present invention. Unit 12 is powered by a source 18, such as an internal battery pack, which can be periodically recharged using a peripheral AC line cord. An isolated power supply control 158 continuously checks the voltage from the battery pack 18, advises the operator when it is time for re-charging, and disables all RF output functions when the battery voltage drops below a minimum level. Specifically, direct battery voltage is sensed by amplifier 160. The output of amplifier 160 is monitored by a display driver circuit 162. Circuit 162 is wired to illuminate the low LED 164 when the battery voltage is below a defined voltage level and requires re-charging, to illuminate the OK LED 33 when the battery voltage is at an acceptable voltage level, and to flash the high LED 34 if the battery voltage is sensed to be higher than an acceptable limit. If the battery voltage is OK, an output signal 170 is sent to the power level controller 44, enabling the RF power enable circuitry.

The monitoring of battery voltage is very important because it assures that electronic circuits are being powered with adequate supply voltage, that treatment RF dosage is not compromised due to low battery voltage, and that electronic circuits (including battery) are not stressed or damaged due to excessively high or low battery voltage.

FIGS. 9–13 show preferred embodiments of the applicator 14 of the present invention. As shown in FIGS. 9–13, the applicator 14 is a monolithic assembly of one or more circuits having a fixed capacitance. This important feature renders the device substantially unaffected by impedance, capacitance and other related affects associated with locating an electromagnetic energy applicator in proximity to a patient's body. Unlike prior art devices which require manual adjustment of the capacitor(s) in the applicator at the treatment site, the present invention has a capacitance fixed by the manufacturer, thereby rendering the device user friendly. Each applicator includes one or more circuits (such as etched copper printed circuit, stamped wire circuit, etc.) formed on a single substrate, such as an assembly comprising one or more circuit boards. Preferably, the circuits are etched or otherwise located on opposite surfaces of a single circuit board.

Referring to one embodiment of the present applicator shown in FIGS. 9–11, applicator 14 includes a single circuit 174 that is laminated between insulating sheets of flexible Kapton 178, or similar material with high dielectric properties. Circuit 174 includes an etched inductor 180, a fixed capacitor 192 connected in parallel with inductor 180, a signal detector 182, and a body proximity sensor 184. A ground plane 176, such as a solid RF copper shield, is located directly below the first etched printed circuit 174. Circuit 174 and plane 176 are brought out to a connection interface 186 to which a flexible and shielded, multi-conductor cable 188 is permanently attached. Connection to the generator unit 12 is made through connector 190, shown in FIG. 10. That composite assembly defines the completed applicator 14.

Figure 12:
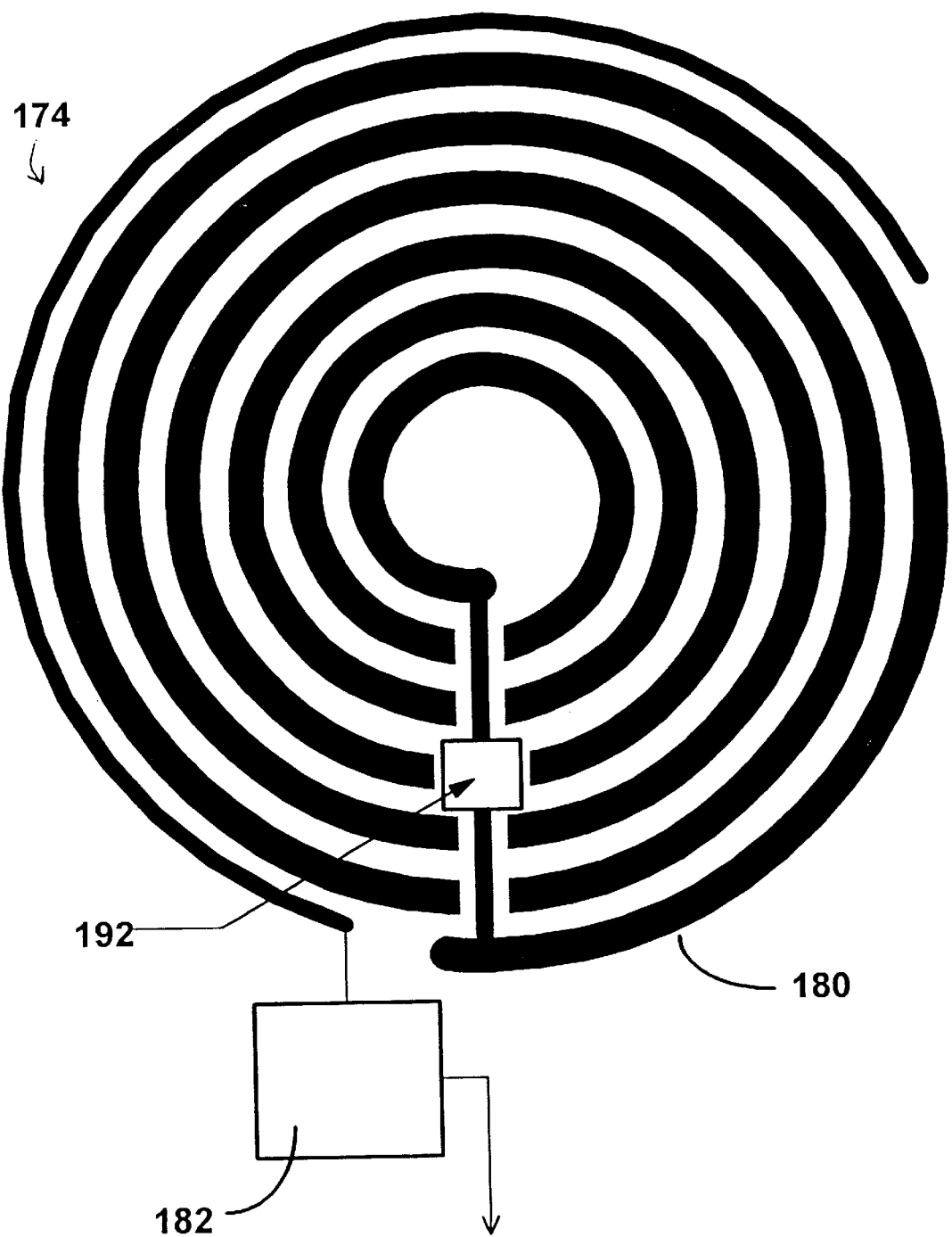
FIG. 12 is a plan view of another embodiment of the applicator of the apparatus of FIG. 1.
Figure 13:
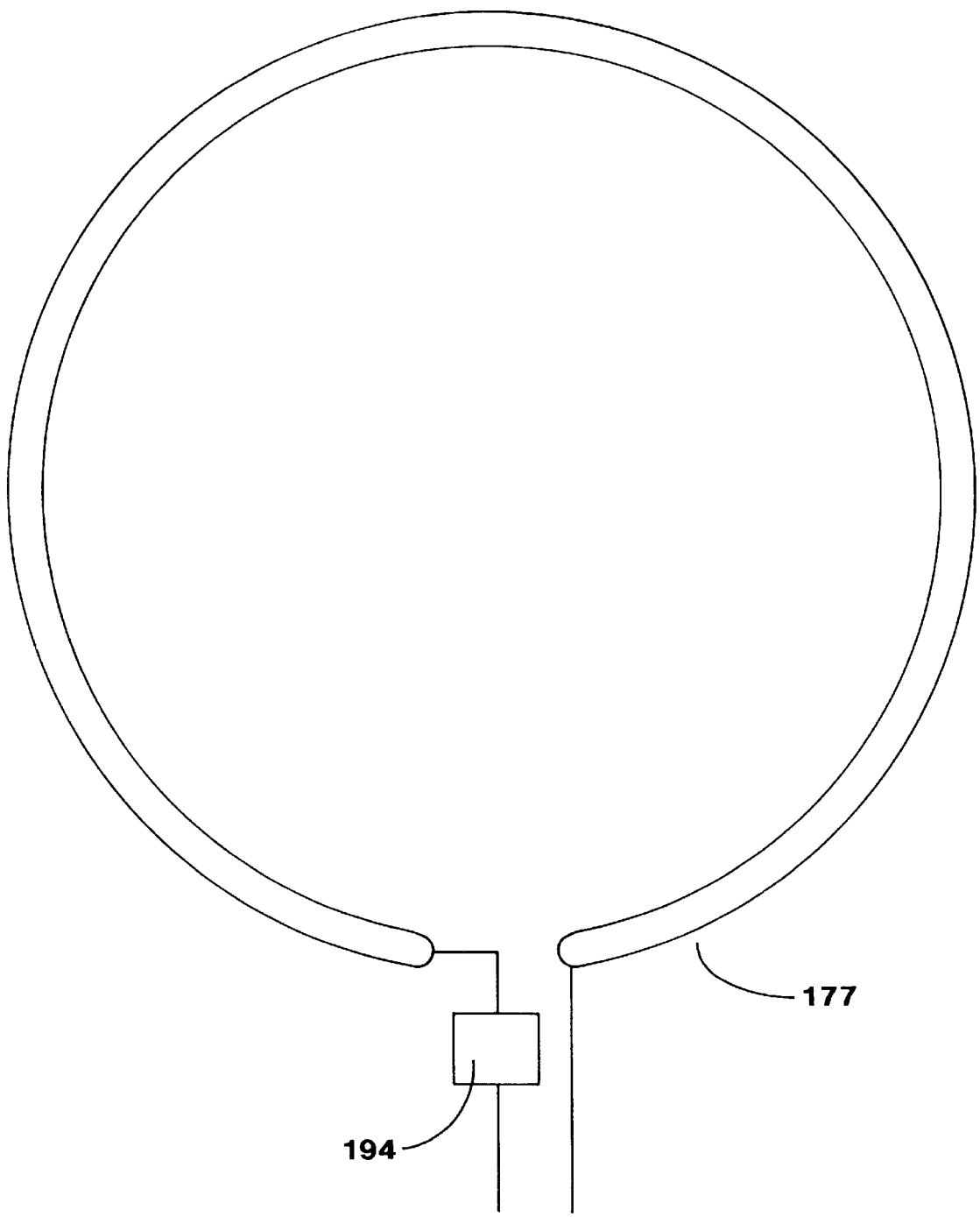
FIG. 13 is a bottom view of the applicator of FIG. 12.

FIGS. 12 and 13 show an alternative embodiment of the applicator described above having multiple circuits 174 and 177. In the applicator 14, the upper circuit 174 forms the secondary of an RF transformer. The primary circuit 177 is etched on the other side of this two sided board. The upper circuit 174 (secondary), which is a multi-turn spiral, has a fixed, surface mount capacitor 192 connected in parallel with it to form a tank circuit resonant at 27.12 Mhz. Circuit 177 (primary), comprising a single turn, has a fixed, surface mount capacitor 194 connected in series. The ends of this series-resonant circuit are brought out to a connection interface 186 from which it is then connected to controller 44 and RF amplifier 36. The function of the LC tank circuit is to radiate a pulsed RF energy in the form of a closed and concentrated RF electromagnetic energy field.

Circuit 174 also includes detector 182. Detector 182 is brought out to the connection interface 186 and serves as an RF energy measuring element, and as such, measures, monitors, regulates and controls the magnitude of the pulsed electromagnetic energy field, or treatment dosage, as it radiates out from the applicator. The returned signal level from detector 182 is sent to the power level controller 44, where it is used as a feedback control signal. If at any time, detector 182 measures radiated electromagnetic energy output level above or below an acceptable RF level, a service required lamp (FIG. 3) will flash and the power level controller disables the RF energy output.

It should be understood that any appropriate detector 182, such as a germanium diode, may be used without departing from the scope of the present invention.

Applicator 14 also includes a body proximity sensor switch 184. Switch 184 confirms that applicator 14 is in place and attached to the patient and that the emitted pulsed RF energy field is being efficiently coupled from the applicator 14 to the patient. In use, applicator 14 is either placed under the patient, in close proximity to the patient's wound, or wrapped around the limb of a patient and attached with fasteners, or is placed over a wound, again being held in place with fasteners. If applicator 14 is secured correctly, the body proximity sensor switch 184 closes, indicating to the power level controller 44 that applicator 14 is in place, and a lamp indicating applicator in place 27 is activated. If any time during treatment, the body proximity sensor switch 184 opens, indicating that applicator 14 is not in body contact, a check applicator 28 lamp flashes and the power level controller 44 disables the RF energy output.

Unlike many prior art devices, which are magnetic field based and, in some instances prevent the electrical field component of the electromagnetic energy from being transmitted, the present invention relies on electrical field-based information for effective operation. Electrical field strength detector 182 included in each applicator 14 produces a DC voltage as a function of the actual field strength being transmitted from applicator 14. This DC voltage is transmitted in a reverse manner (antidromically) through the same coaxial cable 188 which carries the RF signal from amplifier 36 to applicator 14. In this manner, only one cable is required to carry and process both the RF power and RF detection signals. This represents a substantial improvement over the prior art, none of which have a signal detection means at the level of the actual RF signal output, and none of which carry this detection signal over the same cable as used for transmitting the RF signal.

In the RF generator 30, this DC voltage (detection signal 118) is compared to a reference DC voltage which represents the desired field strength. The output of the comparator 120, 122 drives suitable amplifiers 100 which control the DC power supply voltage to the RF circuits, thus controlling the forward RF power. The field strength, being a function of the RF power, is thereby accurately controlled and maintained. This is a significant improvement not found in existing devices, and represents the first capability to accurately deliver, monitor and automatically control the actual RF power delivered to the tissue being treated, thereby ensuring an accurate dosage delivery and dosimetry system.

The circuits are located on a single substrate, such as a circuit board. The substrate is preferably thin and may be flexible or rigid and constructed from one or more sheets. When multiple circuits are included (FIGS. 12 and 13), the circuits are preferably concentrically located on the substrate. While it is not necessarily required that the circuits be exactly concentric, best results are achieved when the two circuits are as close to concentrically positioned as possible.

Preferably, the applicator 14 is approximately 6 inches by 8 inches by less than 1 inch thick, and is housed within a waterproof outer covering. The outer surface is water proof, bacterial resistant and designed to be placed directly on the patient or on top of any standard dressings used over the area to be treated. The generating unit 12 is about 2.5 inches by 5 inches by 8 inches, and has a weight of less than three pounds. In a preferred embodiment, unit 12 includes a display panel which contains the operating switch or button, a treatment time remaining display, a light which is on during treatment to notify the operator that treatment is occurring, and a service light which comes on if the unit needs servicing.

Unit 12 is a hand-held one, which is easily transported from site to site. Applicators 14 are self supporting structures which do not require any mechanical support structure for positioning. Indeed, the only means connecting the applicator 14 to the generating unit 12 is a cable.

Reference throughout this description to LEDs and other specific indicators was made for descriptive purposes only. It is understood that other indicating means for informing users of operational conditions are interchangeable with the specific indicators disclosed herein.

Treatment dosages of electromagnetic energy are applied as follows. The control logic circuit is programmed with treatment profiles which enable the oscillator to provide a treatment dosage of about 1–300 mw/cm$^2$. The preferred treatment profile is administered twice a day, eight to twelve hours between treatments, for thirty minutes. Indeed, the unit is preferably factory preset to deliver treatment for thirty minutes and requires no operator adjustment. When ready, the "start/stop" button is pressed. When this button is pressed, the indicator light indicates therapy has started and an electromagnetic energy dosage is generated and delivered to the treatment site. The electrical field at the treatment site is continuously monitored, with information being delivered back to the generating unit to control the dosage level. At the end of thirty minutes, the unit turns itself off and the power indicator light becomes dark.

The following are representative examples of treatments administered using the present invention.

EXAMPLE 1

This example describes treatment on fibroblasts, a cell type critical to the wound healing process, using the present invention. Immortalized (Rat-2) or primary (human SA-1) fibroblasts were plated 24 hours prior to treatment in 96-well trays at initial densities from 500–10,000 cells per well in Dulbecco's modified Eagle's medium supplemented with high (10% horse, 5% fetal calf) or low (0,5% fetal calf) serum. Cells were treated either with the present invention or a control. The treatment parameters for the present invention, i.e., pulse duration, peak power, average power (dose) and rate of pulse presentation, were systematically varied. Optimal average power, pulse duration and repetition rate were shown to be about 32 mw/cm$^2$, about 32 µs, and a mean of about 1,000 pps respectively. Systematic changes in proliferative response as a function of changes in parameter value were found for all conditions. These results demonstrate that specific characteristics of the present invention critically influence the efficacy of response, and provide a clear picture of the optimum control logic parameters necessary for efficacious treatment of wounds in a clinical setting.

EXAMPLE 2

This example evidences the dose- and time-dependent effects of treatment using the present invention on Rat-2 immortalized and SA-1 human primary fibroblasts in culture. Cells plated in multi-well trays at a series of densities in medium supplemented with serum at different concentrations were treated using the present invention at an average dose of between about 0–178 mw/cm$^2$. Other cells were treated with 32 mw/cm$^2$ for 0 to 60 minutes. After 24 hrs, cells were quantitated directly, via mitochondrial enzyme activity or crystal violet staining. When control logic circuits were preset to provide a pulse width of 32 microseconds and a pulse rate of about 600–1,000 pulses per second, proliferation was significantly enhanced (50–200%, p<0.001) with an $ED_{50}$ of 15 mw/cm$^2$ and an $ED_{99}$ of 32 mw/cm$^2$. Maximal proliferation occurred following 15–60 min treatment time with ½-maximal effects at 8 min. These results reveal optimal and minimal doses and times of treatment to trigger proliferation response.

EXAMPLE 3

Example 3 describes a novel and proprietary method of accelerating healing to closure of chronic cutaneous wounds. It is clear that effects seen clinically and in vitro are based upon enhanced pro-proliferative effects. Evidence for a specific mechanism for enhanced cell proliferation has now been obtained. Rat-2 immortalized or SA-1 human primary fibroblasts seeded at initial densities from 500–10,000 cells per well were treated with a 32 mw/cm$^2$ dose or sham treated (naive). At times ranging from 0 to 16 hr posttreatment, medium was removed from wells containing treated cells and transferred to wells containing naive cells. To define positive and negative controls, respectively, some treated cells were kept in medium throughout, and some naive cells were not exposed to treated medium. At 24 hr posttreatment, all cells were crystal violet stained and quantified spectrophotometrically. Modest proliferation above control levels was observed for cells treated with the present invention, even if medium was removed immediately after treatment, but larger and time-dependent increases in numbers of cells treated with the present invention were obtained if medium was left on those cells for 5–16 hours. Proliferation of naive cells was also observed if they received treated cell medium 0–16 hr after treatment. These studies show that diffusible entities promoting cell proliferation are released into and conditions cell culture medium upon treatment using the present invention.

EXAMPLE 4

This example describes a clinical study wherein a novel, noninvasive endogenous pharmacotherapeutic wound treatment was realized. Twenty High or Moderate Risk patients with Stage II, III or IV pressure ulcers were entered into this study. This group presented with very severe wounds relative to the total pressure sore population. Mean study wound surface area was 17.6±2.1, compared to a population average of 6.6±1.3, and all patients were severely compromised in nutritional and medical status. Patients were treated for thirty minutes twice daily, with a dose equal to about 32 mw/cm$^2$ measured at a distance of about 6 cm from the applicator surface. All patients responded positively to the present treatment. Stage II wounds closed in about 3–5 weeks, compared to a norm of about 8 weeks for smaller wounds. Stage III and Stage IV wounds showed similar acceleration of wound healing. Average rate to closure was about 28 mm$^2$/day, compared to population norms of 3–9 mm$^2$/day for patients not treated with the present method. A highly novel finding is that tissue repair was stimulated through several layers of the wound bed, with rapid loss of necrotic tissue and simultaneous robust granulation. According to these data, the present invention reduces the time associated with wound healing by 50%.

The above examples are provided by way of illustration, and are not intended to limit the scope of the present invention.

It should be understood that references to wound treatment are not limited to the induction of granulation, epitheliation and vascularization at a wound site, but also includes restoring nutrient load to a wound site, thereby inducing synthesis of growth factors, inducing the synthesis, proliferation and release of fibroblasts, epithelial, endothelial, vascular, muscle and neuronal cell types, inducing macrophage activity in a wound site, increasing mitogenic stimuli, increasing concentration of and inducing effective biological activity of growth factors within a wound site, delivering multiple growth factor therapy to a tissue, altering activity of cell cycle dependent proteins, inducing synthesis and activity of signal transduction molecules, and inducing gene expression in a tissue, among other events. Further, while the present invention is described in terms of human treatment methods, it should be understood that treatment, as used herein, encompasses laboratory applications and procedures as well as veterinary applications and the like.

From the foregoing, it will be appreciated by those skilled in the art that the present invention provides a particularly effective and advantageous method of and apparatus for overcoming many of the limitations associated with the treatment of patients using electromagnetic energy. It will also be readily appreciated by one with ordinary skill in the art to use the method and apparatus of the present invention in other applications, such as veterinary applications.

Although certain presently preferred embodiments of the present invention have been specifically described herein, it will be apparent to those skilled in the art to which the invention pertains that variations and modifications of the various embodiments shown and described herein may be made without departing from the spirit and scope of the invention.

We claim:

1. An electromagnetic energy treatment apparatus comprising means for generating pulsed high frequency signs and at least one self-supporting applicator having said pulsed high frequency signals as an input for inducing said pulsed high frequency signals into a target area, wherein said applicator is solely connected to said generating means by a cable, wherein said applicator is flexible, and wherein said applicator comprises a circuit means for delivering an electromagnetic treatment dosage, and wherein said circuit means has a fixed capacitance while delivering said energy treatment dosage.

2. An electromagnetic energy treatment apparatus, comprising:
    means for generating pulsed high frequency signals;
    at least one self-supporting applicator having said pulsed high frequency signals as an input for inducing said pulsed high frequency signals into a target area, wherein said applicator is solely connected to said generating means by a cable; and
    means for securing said applicator to a patient, and wherein said applicator comprises a circuit means for delivering an electromagnetic treatment dosage, and wherein said circuit means has a fixed capacitance while delivering said energy treatment dosage.

3. An electromagnetic energy treatment apparatus, comprising:
    means for generating pulsed high frequency signals; and
    at least one self-supporting applicator having said pulsed high frequency signals as an input for inducing said pulsed high frequency signals into a target area, wherein said at least one self supporting applicator comprises a circuit means for delivering an electromagnetic energy treatment dosage, and wherein said circuit means has a fixed capacitance while delivering said energy treatment dosage.

4. Apparatus according to claim 3, wherein said circuit means further comprises a first circuit and a second circuit positioned proximate said first circuit, and wherein said first and second circuits have fixed capacitance.

5. Apparatus according to claim 4, wherein said first circuit has a first fixed capacitor, and wherein said second circuit has a second fixed capacitor.

6. Apparatus according to claim 3, wherein said circuit means further comprises a coil, a fixed capacitor configured with said coil, and a ground plane located directly below said coil.

7. Apparatus according to claim 3, wherein said circuit means comprises a secondary circuit and a primary circuit positioned proximate said secondary circuit, wherein said secondary circuit comprises an inductor and a fixed capacitor configured as a tank circuit, and wherein said primary circuit comprises an inductor and a capacitor in series with said inductor.

8. Apparatus according to claim 3, wherein said circuit means further comprises a substrate and multiple circuits for inducing a treatment dosage, wherein said multiple circuits are generally concentrically located on said substrate.

9. Apparatus according to claim 8, wherein said multiple circuits further comprise a secondary circuit and a primary circuit positioned proximate said secondary circuit, wherein said secondary circuit comprises an inductor and a fixed capacitor configured as a tank circuit, and wherein said primary circuit comprises an inductor and a capacitor in series with said conductor.

10. Apparatus according to claim 8, wherein said multiple circuits further comprise a coil, a fixed capacitor configured with said coil, and a ground plane located beneath said coil.

11. Apparatus according to claim 8, wherein said multiple circuits further comprise a first circuit printed on said substrate and a second circuit printed on said substrate.

12. Apparatus according to claim 11, wherein said substrate has an upper surface and a lower surface, and wherein said first circuit is printed on said upper surface and said second circuit is printed on said lower surface.

13. Apparatus according to claim 8, wherein said substrate is flexible.

14. Apparatus according to claim 13, wherein said substrate further comprises multiple sheets, and wherein said multiple circuits are positioned between said multiple sheets.

15. Apparatus according to claim 14, wherein said sheets are made of a high dielectric material.

16. Apparatus according to claim 3, wherein said circuit means further comprises means for radiating electromagnetic energy into a target area and means for monitoring a position of said radiating means.

17. Apparatus according to claim 16, wherein said monitoring means further comprises a proximity sensor switch.

18. Apparatus according to claim 16, wherein said radiating means further comprises a substrate and at least one circuit carried by said substrate, and wherein said monitoring means is located on said radiating means.

19. Apparatus according to claim 3, wherein said circuit means further comprises means for radiating electromagnetic energy into a treatment area, said radiating means including a substrate and at least one circuit carried by said substrate, means located proximate said at least one circuit for directly detecting the electromagnetic energy emitted by said radiating means, and means located proximate said substrate for monitoring a position of said radiating means.

20. Apparatus according to claim 3, wherein said circuit means further comprises a rigid member comprising one or more rigid sheets, wherein said circuit means is carried by said rigid member.

21. Apparatus according to claim 20, wherein said circuit means further comprises a secondary circuit and a primary circuit positioned proximate said secondary circuit, wherein said secondary circuit comprises an inductor and a fixed capacitor configured as a tank circuit, and wherein said primary circuit comprises an inductor and a capacitor in series with said conductor.

22. An electromagnetic energy treatment apparatus, comprising:

means for generating pulsed high frequency signals; and
at least one self-supporting applicator having said pulsed high frequency signals as an input for inducing said pulsed high frequency signals into a target area, wherein said at least one self supporting applicator comprises a circuit means, wherein said circuit means comprises means for radiating electromagnetic energy into a target area and means for continuously detecting the electromagnetic energy emitted by said radiating means.

23. Apparatus according to claim 22, wherein said detecting means is a field strength sensing and measuring circuit.

24. Apparatus according to claim 22, wherein said radiating means further comprises a substrate and at least one circuit carried by said substrate, and wherein said detecting means is positioned on said substrate.

25. An electromagnetic energy treatment apparatus comprising means for generating pulsed high frequency signals and at least one self-supporting applicator having said pulsed high frequency signals as an input for inducing said pulsed high frequency signals into a target area, wherein said applicator is solely connected to said generating means by a cable, and wherein said at least one self-supporting applicator comprises multiple applicators having said pulsed high frequency signals as inputs for inducing said pulsed high frequency signals into a target site.

26. Apparatus according to claim 25, wherein said applicators operate simultaneously.

27. Apparatus according to claim 25, wherein said generating means further comprises means for simultaneously delivering different signals to each applicator.

28. Apparatus according to claim 25, wherein said applicators operate independently.

29. Apparatus according to claim 25, wherein said generating means further comprises means for independently delivering different signals to each applicator.

30. An electomagnetic energy treatment apparatus comprising:

means for generating pulsed high frequency signals, wherein said generating means comprises a pulse generator for generating energy pulses, at least one amplifier connected to said generator for amplifying said energy pulses into said pulsed high frequency signal output, and automatic control means for automatically controlling said pulsed high frequency signal output, wherein said control means comprises at least one power level controller connected to said at least one amplifier and at least one control circuit connected to said power level controller for automatically controlling said pulsed high frequency signal output; and
at least one self-supporting applicator having said pulsed high frequency signals as an input for inducing said pulsed high frequency signals into a target area, wherein said applicator is solely connected to said generating means by a cable.

31. Apparatus according to claim 30, wherein said pulse generator further comprises a pulse rate timer circuit for generating a time setting output, a pulse width timer circuit for receiving said time setting output and for producing a single, fixed width, fixed shaped enabling pulse, and a high frequency oscillator for receiving said enabling pulse and for generating high frequency energy signals.

32. Apparatus according to claim 31, wherein said at least one control circuit further comprises a pulse shaper and repetition controller circuit connected to said pulse generator and to said power level controller.

33. Apparatus according to claim 30, wherein said at least one control circuit further comprises a control logic circuit.

34. Apparatus according to claim 30, wherein said at least one control circuit further comprises a programmable means for automatically controlling characteristics of said pulsed high frequency signal output generated by said generating means, said programmable means having outputs connected to said power level controller and said pulse generator.

35. Apparatus according to claim 34, wherein said programmable means further comprises a programmable logic array and means connected to said array for selecting a pulse profile from multiple profiles stored in said array.

36. Apparatus according to claim 34, further comprising at least one treatment selector means for selecting a desired treatment profile.

37. Apparatus according to claim 30, wherein said at least one circuit further comprises a power measuring circuit means for measuring said pulsed high frequency signal output from said amplifier of said generating means and for generating an output, and wherein said power level controller further comprises means for comparing said output of said power measuring circuit means to a predetermined value and means for disabling said generating means when said output of said power measuring circuit means exceeds said predetermined values.

38. Apparatus according to claim 37, wherein said power controller further comprises means for triggering alarms when said generating means is disabled.

39. Apparatus according to claim 30, wherein said at least one circuit further comprises means located proximate to said applicator for measuring an energy output emitted from said applicator and for generating a feedback signal corresponding to said measured output.

40. Apparatus according to claim 39, wherein said power level controller further comprises means for comparing said feedback signal to predetermined values and means for disabling said generating means when said feedback signal fails said comparison.

41. Apparatus according to claim 39, wherein said power level controller further comprises means for adjusting an output of said generator in response to said feedback signal.

42. Apparatus according to claim 39, wherein said power controller further comprises means for triggering alarms when said generating means is disabled.

43. Apparatus according to claim 30, wherein said control circuit further comprises treatment timer means for controlling a time period for production of said pulsed high frequency signal output by said generating means.

44. Apparatus according to claim 43, wherein said power level controller further comprises means for disabling said treatment timer means.

45. Apparatus according to claim 44, wherein said treatment timer means is preset to clock a predetermined treatment dosage.

46. Apparatus according to claim 44, further comprising a treatment selector means operationally connected to said treatment timer means, wherein a desired treatment time is selected using said treatment selector means.

47. Apparatus according to claim 30, further comprising a battery power supply connected to said power level controller, and wherein said at least one control circuit further comprises means for monitoring an output of said power supply and for disabling operation of said generating means when low power is detected.

48. An electromagnetic energy treatment apparatus comprising:
means for generating pulsed high frequency signals comprising:
automatic control means for automatically controlling said pulsed high frequency signal output, wherein said control means comprises
at least one power level controller connected to said at least one amplifier and at least one control circuit connected to said power level controller for automatically controlling said pulsed high frequency signal output said at least one control circuit comprising;
means for controlling treatment time;
a power measuring circuit means having an input connected to said amplifier;
a power supply control circuit means;
means for monitoring placement of said applicator having an output connected to said power level controller; and
means for detecting strength of treatment energy emitted by said applicator,
wherein each of said means has an output connected to said power level controller;
a pulse generator for generating energy pulses; and
at least one amplifier connected to said generator for amplifying said energy pulses into said pulsed high frequency signal output; and
at least one self-supporting applicator having said pulsed high frequency signals as an input for inducing said pulsed high frequency signals into a target area, wherein said applicator is solely connected to said generating means by a cable.

49. An electromagnetic energy treatment apparatus comprising:
means for generating pulsed high frequency signals comprising:
automatic control means for automatically controlling said pulsed high frequency signal output, wherein said control means comprises
at least one power level controller connected to said at least one amplifier and at least one control circuit connect ed to said power level controller for automatically controlling said pulsed high frequency signal output said at least one control circuit comprising;
means for controlling treatment time;
a power measuring circuit means having an input connected to said amplifier;
a power supply control circuit means;
means for monitoring placement of said applicator having an output connected to said power level controller;
means for detecting strength of treatment energy emitted by said applicator and
means located on said applicator for monitoring a position of said applicator and for generating a feedback signal corresponding to said position;
wherein each of said means has an output connected to said power level controller;
a pulse generator for generating energy pulses; and
at least one amplifier connected to said generator for amplifying said energy pulses into said pulsed high frequency signal output; and
at least one self-supporting applicator having said pulsed high frequency signals as an input for inducing said pulsed high frequency signals into a target area, wherein said applicator is solely connected to said generating means by a cable.

50. Apparatus according to claim 49, wherein said power level controller further comprises means for actuating an appropriate indicator in response to said feedback signal.

51. Apparatus according to claim 49, wherein said monitoring means is a body proximity sensor switch.

52. An electromagnetic energy treatment apparatus, comprising:

means for generating pulsed high frequency signals;

at least one self-supporting applicator having said pulsed high frequency signals as an input for inducing said pulsed high frequency signals into a target area; and a power supply, wherein said generating means has an input from said power supply and said power supply has an average power output of less than about 3 watts.

53. Apparatus according to claim 52, wherein said power supply has an average power output of less than about 1 watt.

54. An electromagnetic energy treatment apparatus in accordance with claim 52, wherein said power supply is a battery power supply, wherein said generating means has an input from said battery power supply.

55. An electromagnetic energy treatment apparatus in accordance with claim 52, wherein said generating means weighs less than about 3 pounds.

56. An electromagnetic energy treatment apparatus in accordance with claim 52, wherein said generating means has a height of about 8 inches, a length of about 5 inches and a thickness of about 2.5 inches.

\* \* \* \* \*

UNITED STATES PATENT AND TRADEMARK OFFICE
CERTIFICATE OF CORRECTION

PATENT NO. : 6,334,069 B1
DATED : December 25, 2001
INVENTOR(S) : Frank R. George et al.

It is certified that error appears in the above-identified patent and that said Letters Patent is hereby corrected as shown below:

<u>Column 20, claim 1,</u>
Line 29, "signs" should be -- signals --.

<u>Column 24, claim 49,</u>
Line 41, "connect ed" should be -- connected --.
Line 53, insert after the word "applicator" -- , --.

Signed and Sealed this

Nineteenth Day of March, 2002

Attest:

Attesting Officer

JAMES E. ROGAN
*Director of the United States Patent and Trademark Office*